(12) United States Patent
Scholz et al.

(10) Patent No.: US 7,309,519 B2
(45) Date of Patent: *Dec. 18, 2007

(54) FRICTION CONTROL ARTICLES FOR HEALTHCARE APPLICATIONS

(75) Inventors: Matthew T. Scholz, Woodbury, MN (US); Margie A. Crone, Woodbury, MN (US); Nicholas R. Baumann, St. Paul, MN (US); Leon Levitt, Medota Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 136 days.

This patent is subject to a terminal disclaimer.

(21) Appl. No.: 09/982,741

(22) Filed: Oct. 17, 2001

(65) Prior Publication Data

US 2002/0114920 A1    Aug. 22, 2002

Related U.S. Application Data

(63) Continuation-in-part of application No. 09/637,567, filed on Aug. 11, 2000, now Pat. No. 6,610,382, which is a continuation-in-part of application No. 09/166,837, filed on Oct. 5, 1998, now Pat. No. 6,372,323.

(51) Int. Cl.
   *A61B 19/08* (2006.01)
   *B32B 3/30* (2006.01)

(52) U.S. Cl. ............... 428/119; 128/849; 128/852; 128/853; 428/100; 428/104; 428/120; 428/167; 428/172; 442/76; 442/101; 442/327

(58) Field of Classification Search ............... 428/100, 428/104, 119, 120, 167, 172; 442/72, 101, 442/327; 128/852, 853, 849
See application file for complete search history.

(56) References Cited

U.S. PATENT DOCUMENTS

| | | | |
|---|---|---|---|
| 3,266,113 A | | 8/1966 | Flanagan, Jr. |
| 3,585,101 A | | 6/1971 | Stratton et al. |
| 3,654,047 A | | 4/1972 | Berkowitz |
| 3,738,359 A | * | 6/1973 | Lindquist et al. ............ 128/132 |
| 3,972,328 A | * | 8/1976 | Chen .......................... 128/156 |
| 4,204,532 A | * | 5/1980 | Lind et al. ............... 128/132 D |
| 4,290,174 A | | 9/1981 | Kalleberg |
| 4,343,848 A | | 8/1982 | Leonard, Jr. |

(Continued)

FOREIGN PATENT DOCUMENTS

CA            1197745       * 12/1985

(Continued)

*Primary Examiner*—Nasser Ahmad
(74) *Attorney, Agent, or Firm*—Nancy M. Lambert

(57) ABSTRACT

Friction control articles for use in healthcare applications, the articles generally comprising a backing Layer having a first surface and a second surface, where projecting from the first surface of the backing layer is an array of stems, wherein at least a portion of the exterior surface of the stems comprises an elastomeric material. Also disclosed are friction control articles having a coefficient of friction when dry along at least a portion of the first surface of at least 0.6. Multilayered and dual-sided friction control articles are also provided.

24 Claims, 6 Drawing Sheets

U.S. PATENT DOCUMENTS

| | | | |
|---|---|---|---|
| 4,488,918 A | 12/1984 | Jofs | |
| 4,667,661 A | 5/1987 | Scholz et al. | |
| 4,756,786 A | 7/1988 | Malaney | |
| 4,872,243 A | 10/1989 | Fischer | |
| 4,959,265 A | 9/1990 | Wood et al. | |
| 5,005,590 A | 4/1991 | Eldridge, Jr. et al. | |
| 5,059,271 A | 10/1991 | Taub | |
| 5,077,870 A | 1/1992 | Melbye et al. | |
| 5,178,176 A * | 1/1993 | Fetterman | 135/86 |
| 5,201,101 A | 4/1993 | Rouser et al. | |
| 5,234,740 A | 8/1993 | Reeves et al. | |
| 5,302,440 A | 4/1994 | Davis | |
| 5,491,015 A | 2/1996 | Reeves et al. | |
| 5,508,084 A | 4/1996 | Reeves et al. | |
| 5,511,248 A | 4/1996 | Widdemer | |
| 5,607,745 A * | 3/1997 | Ogden | 428/138 |
| 5,676,092 A | 10/1997 | Ortolivo | |
| 5,908,680 A | 6/1999 | Moren et al. | |
| 5,948,707 A * | 9/1999 | Crawley et al. | 442/101 |
| 6,060,009 A | 5/2000 | Welygan et al. | |
| 6,106,922 A * | 8/2000 | Cejka et al. | 428/120 |
| 6,121,143 A | 9/2000 | Messner et al. | |
| 6,190,594 B1 | 2/2001 | Gorman et al. | |
| 6,359,068 B1 | 3/2002 | Moren et al. | |
| 6,372,323 B1 * | 4/2002 | Kobe et al. | 428/119 |
| 6,610,382 B1 * | 8/2003 | Kobe et al. | 428/119 |
| 2002/0114920 A1 | 8/2002 | Scholz et al. | |

FOREIGN PATENT DOCUMENTS

| | | | |
|---|---|---|---|
| GB | 2 037 536 A | | 7/1980 |
| WO | WO 93/04858 | | 3/1993 |
| WO | WO 94/01051 | | 1/1994 |
| WO | WO 97/27775 | * | 8/1997 |
| WO | WO 00/20210 | | 4/2000 |
| WO | WO 02/13638 A2 | | 2/2002 |

* cited by examiner

FRICTION CONTROL ARTICLES FOR HEALTHCARE APPLICATIONS

CROSS REFERENCE TO RELATED APPLICATION

The present application is a continuation-in-part of U.S. Ser. No. 09/637,567, filed Aug. 11, 2000, now U.S. Pat. No. 6,610,382 which is a continuation-in-part of U.S. Ser. No. 09/166,837, filed Oct. 5, 1998, now U.S. Pat. No. 6,372,323.

FIELD OF THE INVENTION

The present invention is directed to friction control articles, including articles useful in medical applications, having a pleasant and soft feel, high friction properties, and good performance in wet and dry conditions.

BACKGROUND OF THE INVENTION

The development of enhanced grip and anti-slip surfaces typically centers around the materials and the surface topology of the article. Common materials include natural and synthetic rubbers, styrenic block co-polymers, latex, ethylene vinyl acetate, ethylene-propylene rubber, polyurethane, polyester co-polymers, polyimides, and the like. The surface topology can range from smooth to having exaggerated gripping structures. U.S. Pat. No. 3,585,101 discloses a thin sheet of a soft, ductile, flexible material, such as aluminum, brass, plastic or the like, having a knurled pattern embossed to provide an improved gripping surface. The sheet can be applied to solid objects using an adhesive.

U.S. Pat. No. 4,488,918 discloses a plastic film having a non-slip surface comprising spaced, random patterns of rigid peaks and ridges formed of a second thermoplastic material co-extruded with and bonded to a plastic film. The surface has a pattern of relatively high, sharp, irregular plastic peaks and ridges, sufficiently sharp, hard and rough to effect a mechanical gripping with other surfaces.

U.S. Pat. No. 5,234,740 discloses a slip control surface with a structured surface. The structured surface includes an array of protrusions, typically triangular pyramids. The patent discloses that the sheeting may be applied to the handles of athletic equipment such as softball bats, golf clubs, tennis, racquetball, squash, badminton racquets, as well as the handles of tools.

In medical and other healthcare environments, draping articles are often used to cover irregular surfaces onto which instruments and other surgical and medical implements are placed. It would be desirable to secure such implements to the surfaces of such drapes for temporary placement during a procedure without the need for adhesives (which can leave residue) or without the use of magnets (which can magnetize metal instruments). It would also be desirable to have a multi-purpose, conformable high friction surface that can be readily sterilized and can be used in a multitude of applications in healthcare facilities.

SUMMARY OF THE INVENTION

The present invention relates to improved friction control or gripping surfaces that have a pleasant and soft feel, high frictional properties and good gripping performance in both wet and dry conditions. The gripping surfaces are generally soft surfaces having an array of flexible, generally upstanding stems of a variety of shapes produced from a elastomeric, generally thermoplastic, compositions. By "generally upstanding" it is meant that the stems protrude in a planar direction away from the gripping surface. The stems may protrude upward from the surface at generally normal angles, or the stems may protrude at angles away from the surface (e.g., at a forty-five degree angle), thereby imparting a directional frictional performance (i.e., the surface "grips" better when engaged from one direction than another). The stems may also be of a irregular shape such that they may not protrude any one uniform angle. The size, spatial distribution, flexibility of the stems, stem array pattern, and the properties of the elastomer material all contribute to the soft feel of the surface, its ease of draping, and its gripping performance under wet and dry conditions. The various embodiments of the friction or slip control surfaces may include micro-channels, an absorbent layer and hydrophilic/hydrophobic regions all for directing fluids away from the upstanding stems, leaving them dry and providing high frictional performance even in wet conditions. The slip control articles may be formed in a sheet structure, such as a single or double-sided drape, a bed or chair pad, or a wrap that can be applied to another article. The slip control articles may also be incorporated directly into a variety of molded or manufactured articles.

In specific embodiments, the slip control article can comprise a backing layer that has a first surface with an array of stems, the density of which about the surface of the article will be at least 15.5 stems/centimeter$^2$ (100 stems per square inch), and more typically at least 54 stems/centimeter$^2$ (350 stems per square inch) and a second surface. Preferably, for most healthcare applications, the stem density will be greater than about 78 stems/centimeter$^2$ (500 stems per square inch). At least a portion of an exterior surface of the upstanding stems contains an elastomeric material. The stems will typically have an aspect ratio (stem height: stem diameter) of at least 1.25, and preferably at least 1.5, more preferably at least 2.0, most preferably greater than 3.0. The first surface will typically have a static coefficient of friction when dry of at least 0.6 and a static coefficient of friction when wet within 20% of the static coefficient of friction when dry, preferably within 80 or 90% or more, such that the frictional properties do not substantially degrade when water or other fluid is present. In embodiments that call for a mating of two friction control articles or surfaces, the first surface also will typically have a peel strength and a tensile strength of substantially zero when engaged with another slip control surface.

In other embodiments, an array of generally upstanding stems comprising an elastomeric material is also formed on a second surface of the backing layer. The second surface will typically have a static coefficient of friction when dry of at least 0.6 and a static coefficient of friction when wet within 20% of the static coefficient of friction when dry, preferably within 80 or 90% or more. And, like the first surface, the second surface will have a peel strength and a tensile strength of substantially zero when engaged with another slip control surface where it is employed in a use that calls for mating two such articles or surfaces together.

In still other embodiments, the static coefficient of friction when dry is at least 1.0, more preferably at least 2.0. The first surface has a dynamic shear strength of at least 23,268 dynes/centimeter$^2$ (5.4 ounces/inch$^2$), and preferably more than 43,090 dynes/centimeter$^2$ (10 ounces/inch$^2$), and more preferably at least 77,562 dynes/centimeter$^2$ (18 ounces/inch$^2$) and most preferably at least 107,725 dynes/centimeter$^2$ (25 ounces/inch$^2$) when engaged with another slip control surface at a pressure of about 53 grams/6.45 centimeter$^2$. The high shear forces are due primarily to the frictional properties of the elastomeric materials, not a mechanical interlock of the stems, such as on a mechanical fastener.

The backing (or base) layer may be integrated with other layers to form a multilayer base or backing construction. Such additional layers may include, for example, a reinforcing web, a foam layer, a substantially inelastic polymeric layer, or an adhesive or foamed adhesive layer, depending on the application of the slip control article. In one embodiment, the backing layer may be the elastomeric material integrally formed with the generally upstanding stems. The backing layer also may be elastic or inelastic, thick or thin, porous or non-porous, woven or non-woven, and may be formulated with or without an adhesive layer, etc. A preferred embodiment employs a woven netting or scrim material as an intermediate layer. In another embodiment, a non-elastomeric backing layer may form a portion of the stems. Since the backing layer may optionally be extremely thin, the slip control article may be configured as a very thin wrap or gripping tape suitable for use as lightweight gripping applications. Alternatively, the backing layer may be a portion of a molded, extruded or manufactured article. In preferred embodiments, the backing layer will lie between two opposed friction control surfaces in a drape or a mat (or a dual-sided) construction, each with a stem construction. In this way, the drape or mat will have friction control properties on each of these surfaces.

While the above-identified drawing figures set forth preferred embodiments of the invention, other embodiments are also contemplated, as noted in the discussion. In all cases, this disclosure presents the present invention by way of representation and not limitation. It should be understood that numerous other modifications and embodiments can be devised by those skilled in the art which fall within the scope and spirit of the principles of this invention.

DETAILED DESCRIPTION OF PREFERRED EMBODIMENTS

Figure 1:
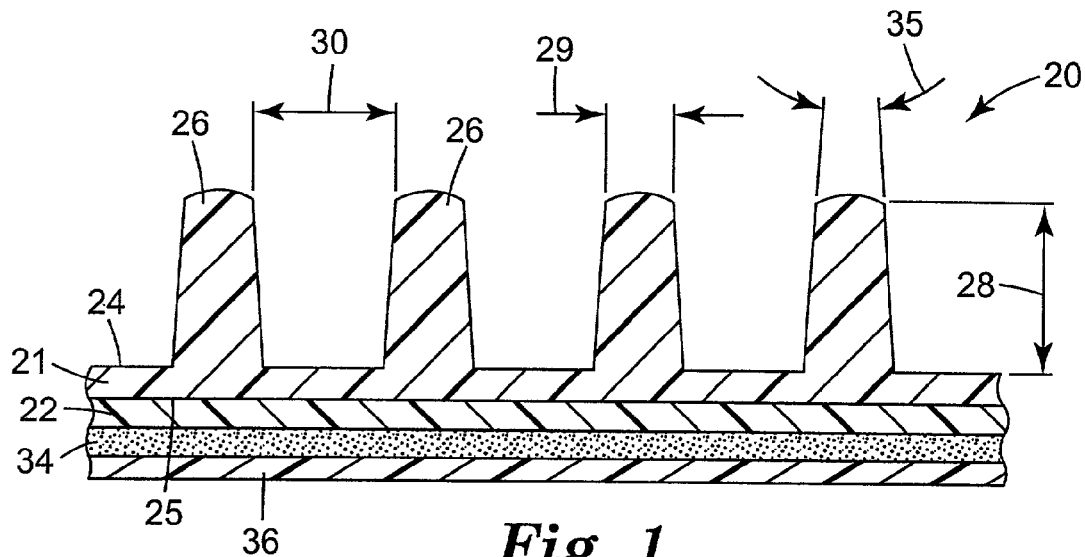
FIG. 1 is a side-sectional view of a friction or slip control article in accordance with the present invention.

FIG. 1 is a side-sectional view of a friction or slip control article 20 in accordance with the present invention. The article 20 includes a backing layer 21 having a first surface 24 with an array of generally upstanding stems 26. The stems may be arranged in a regular or an irregular array. Various patterns of stems may be used, such as hexagonal, diagonal, sinusoidal, etc. The stems 26 are constructed at least in part of an elastomeric material. Preferably, the entire exterior surface of the stems 26 are an elastomeric material. In the embodiment of FIG. 1, the backing layer 21 is integrally formed with the stems 26 of an elastomeric material. The combination of the backing layer 21 and the stems 26 is sometimes referred to as a stem web. Although the illustrated embodiments show the stems 26 as being generally cylindrical, the sides of the stems 26 typically have a slight taper 35 to facilitate removal from the mold. A variety of non-cylindrical shapes can also be utilized, such as truncated cones or pyramids, rectangles, hemispheres, squares, hexagon, octagon, gum drops, and the like.

The slip or friction control article 20 has generally upstanding stems 26 constructed of an elastomeric material and a backing layer 21 to hold the structure together. The backing layer 21, from which the stem directly extend, is typically about 0.05 millimeters to about 0.5 millimeters (0.002 inches to 0.02 inches) thick. The elastomeric properties of the backing layer 21, however, do not fulfill all requirements for some applications, such as when the slip control article 20 is used as a gripping wrap. Therefore, additional backing layers 22, 34, 36 are optionally applied to the second surface 25 to reinforce the backing layer 21 and form a multilayer base or backing construction. The additional backing layer 22 may serve to stabilize and reinforce the slip control article 20, to resist stretching and improving tear resistance, as well as a variety of other functions. Adhesive layer 34 and release liner 36 are optionally provided for attaching the present slip control article 20 to another surface. As used herein, "backing" or "base" layer will be used to refer to the collective backing or base construction. Such a construction may be single or multilayered (such as shown in FIG. 1) having one or more layers that support the generally upstanding stems, although typically at most one of these layers will be integrally formed with the stems.

In some instances, the backing layer 21 is sufficiently thick to bond a reinforcing web during extrusion, such as a sheet of fabric or scrim material, to impart increased tear resistance and tensile strength. The reinforcing web 22 is particularly useful when the slip control article is attached to a flexible substrate via sewing. The reinforcing web may be a foamed or a solid polymeric material. In one embodiment, the it may include a porous and/or absorbent layer, such as layers of fibrous material or fabric scrim which may be woven or nonwoven. A porous material is useful for absorbing moisture and/or directing moisture away from the stems. In one embodiment, the reinforcing web includes a substantially inelastic layer to prevent necking or stretching of the slip control article.

Suitable backing layer materials include thermoplastic polyurethanes, polyvinyl chlorides, polyamides, polyimides, polyolefins (e.g., polyethylene and polypropylene), polyesters (e.g., polyethylene terephthalate), polystyrenes, nylons, acetals, block polymers (e.g., polystyrene materials with elastomeric segments, available from KRATON Polymers Company of Houston, Tex., under the designation KRATON™, polycarbonates, thermoplastic elastomers (e.g., polyolefin, polyester or nylon types) and copolymers and blends thereof. The thermoplastic material may also contain additives, including but not limited to fillers, fibers, antistatic agents, lubricants, wetting agents, foaming agents, surfactants, pigments, dyes, coupling agents, plasticizers, suspending agents, hydrophilic/hydrophobic additives, and the like.

The optional adhesive layer 34 typically comprises an adhesive selected to provide a bond to a substrate article to which the slip control surface is to be applied, such as pressure sensitive adhesives, thermosetting or thermoplastic adhesives, radiation cured adhesives, adhesives activated by solvents, and blends thereof. The adhesive may include filaments. The backing layer can optionally be laminated or impregnated with the adhesive. One adhesive useful in the present invention is Scotch™ Adhesive Transfer Tape 950 available from Minnesota Mining and Manufacturing Company. Many suitable epoxy, urethane, synthetic or natural based rubber and acrylic adhesives are commercially available for this purpose as well. Depending upon the application, the adhesive may releasably bond or permanently bond the slip control article to a surface. For some healthcare applications, and specifically for uses as a general-purpose medical drape, it may be preferred to construct the friction control articles without an adhesive layer and instead construct the article with two sides of the stemmed friction control surface. In this way, packaging waste is reduced and the ease of use is enhanced.

Figure 1A:
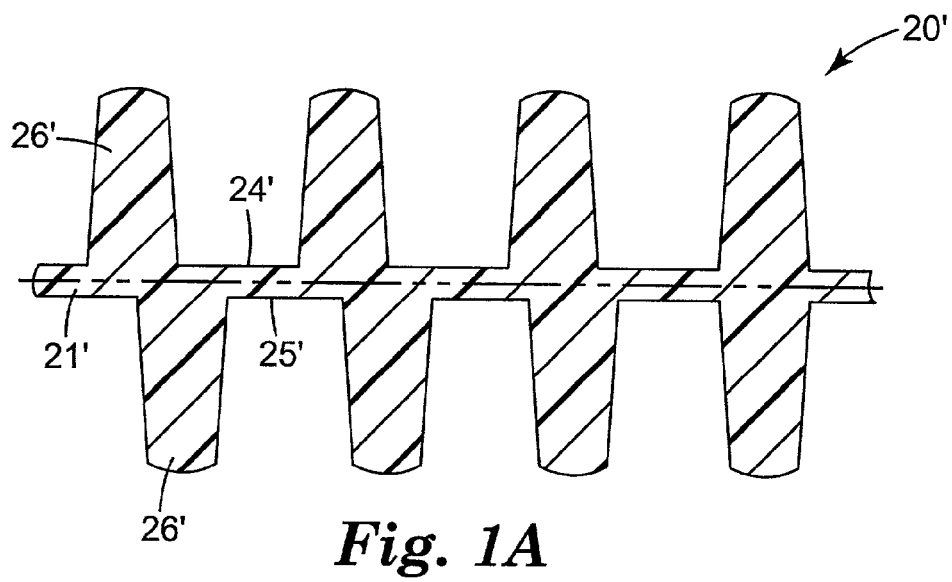
FIG. 1A is a side-sectional view of a two-sided slip control article in accordance with the present invention.

FIG. 1A is a sectional view of a two-sided slip control article 20' as generally illustrated in FIG. 1, without the additional backing layers 22, 34, 36. The article 20' includes a backing layer 21' with an array of generally upstanding stems 26' on both the first and second surfaces 24', 25'. The stems 26' are constructed of a single elastomeric material. In the embodiment of FIG. 1A, the backing layer 21' is integrally formed with the stems 26' of an elastomeric material. In various embodiments, the two sides of the stems of the backing layer may have the same or different shapes and may extend along only a portion of the overall article. In another embodiment, the upper and lower portions may be co-extruded from two different elastomeric materials. Alternatively, the upper and lower portions (which may be made from the same or different material) may be extruded onto both sides of a reinforcing web or scrim material. A two-side slip control article in accordance with the present invention may be formed from the various disclosed embodiments.

Figure 2:
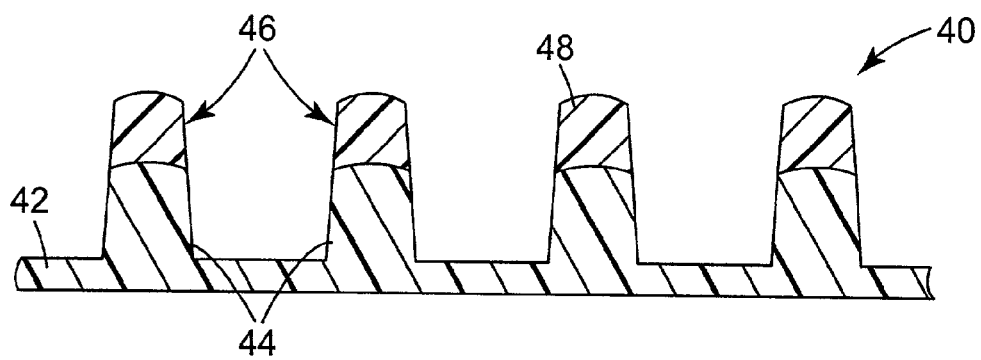
FIG. 2 is a side-sectional view of an alternate slip control article in accordance with the present invention.

FIG. 2 is a side-sectional view of an alternate slip control article 40 in accordance with the invention. Backing layer 42 defines lower portions 44 of the stems 46. The upper portions 48 of the stems 46 are constructed of the elastomeric material. The backing layer 42 and lower portions of the stems 44 may be constructed of a variety of materials, elastomeric or non-elastomeric, depending upon the application for the slip control article 40. At a minimum, the exterior surface of the upper portions 48 are an elastomeric material. In one embodiment, the upper portions 48 of the stems 44 have hydrophobic properties. Hydrophobic properties may be obtained by constructing the upper portions 48 from a hydrophobic material or treating the upper portions 48 to achieve hydrophobic properties. For applications involving contact with non-polar liquids, the upper portions 48 of the stems 46 may be treated to achieve hydrophilic properties (e.g., corona treatment).

Figure 3:
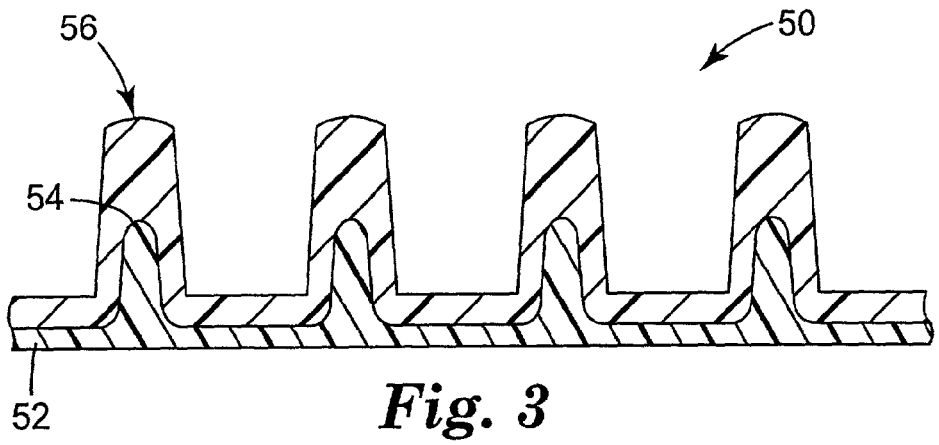
FIG. 3 is a side-sectional view of co-extruded slip control article in accordance with the present invention.

FIG. 3 is a side-sectional view of another alternate slip control article 50 formed by co-extrusion in accordance with the invention. The backing layer 52 protrudes into a center regions 54 to add structural integrity to the elastomeric stems 56. The backing layer 52 is typically a stiffer polymeric material.

Figure 3A:
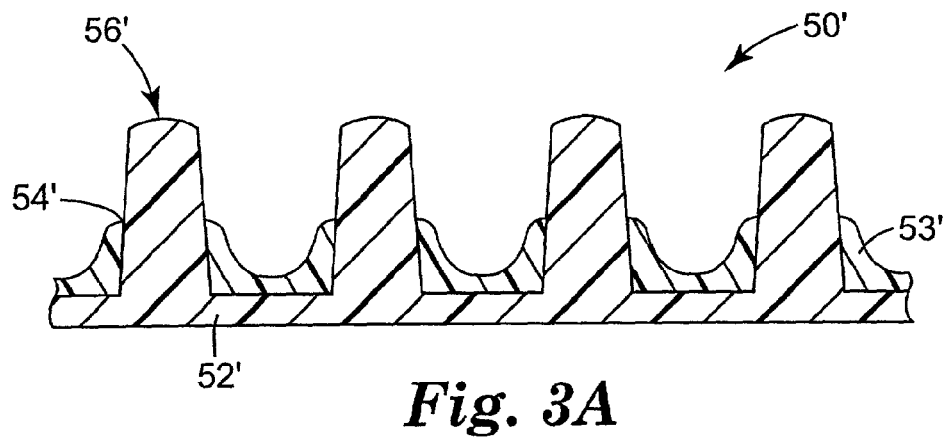
FIG. 3A is a side-sectional view of an alternate co-extruded slip control article in accordance with the present invention.

FIG. 3A is an alternate slip control article 50' formed by co-extrusion in accordance with the invention. The stems 56' and backing layer 52' are constructed of an elastomeric material. The stems 56' protrude through a center region 54' of an additional backing layer 53'. The additional backing layer 53' may provide structural stability, hydrophobic/hydrophilic properties or a variety of other functions. In one embodiment, the additional backing layer 53' may be an elastomeric material with properties different from those used to construct the stems 56'.

Figure 4:
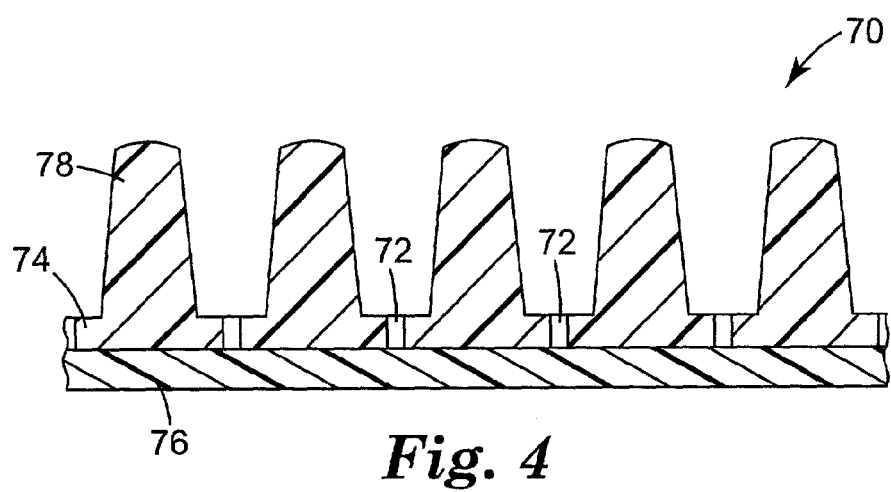
FIG. 4 is a side-sectional view of a slip control article with an absorbent layer on the second surface in accordance with the present invention.

FIG. 4 is a side-sectional view of an slip control article 70 incorporating a plurality of holes 72 through the backing layer 74 in fluid communication with an absorbent layer 76. The absorbent layer 76 draws moisture away from the elastomeric stems 78 to maintain good frictional properties in wet conditions.

Figure 5A:
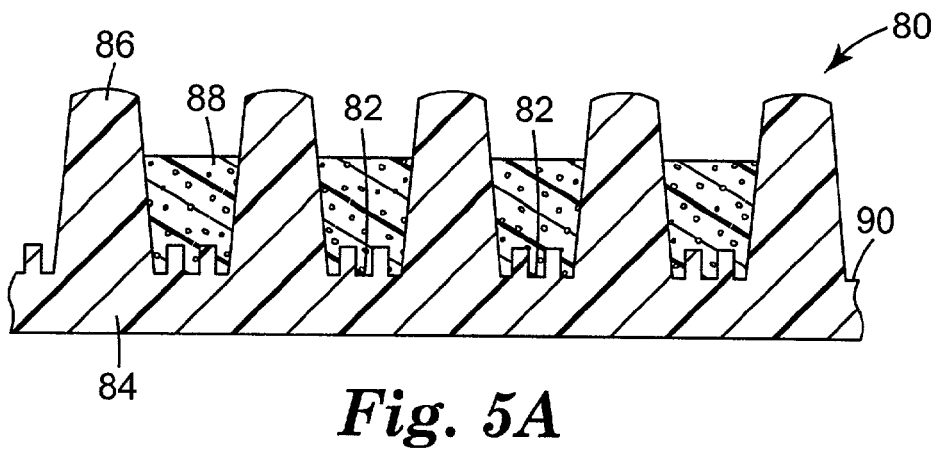
FIG. 5A is a side-sectional view of a slip control article including micro-channels and an absorbent material in accordance with the present invention.
Figure 5B:
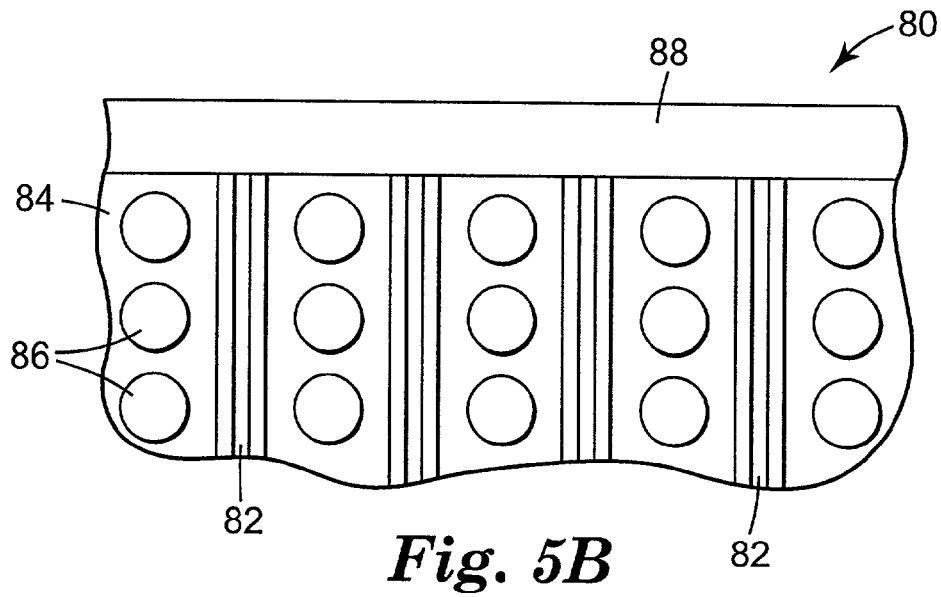
FIG. 5B is a top view of the slip control article of FIG. 5A.

FIGS. 5A and 5B illustrate a slip control article 80 incorporating micro-channels 82 on the backing layer 84 between the upstanding elastomeric stems 86. The micro-channels 82 utilize capillary forces to cause the rapid transport of a fluid in a direction of a driving force. Absorbent layer 88 is located along the first surface 89 of the backing 84 to provide the driving force. Alternatively, the driving force may be gravity and/or hydrophilic areas on the stems 86.

Figure 6:
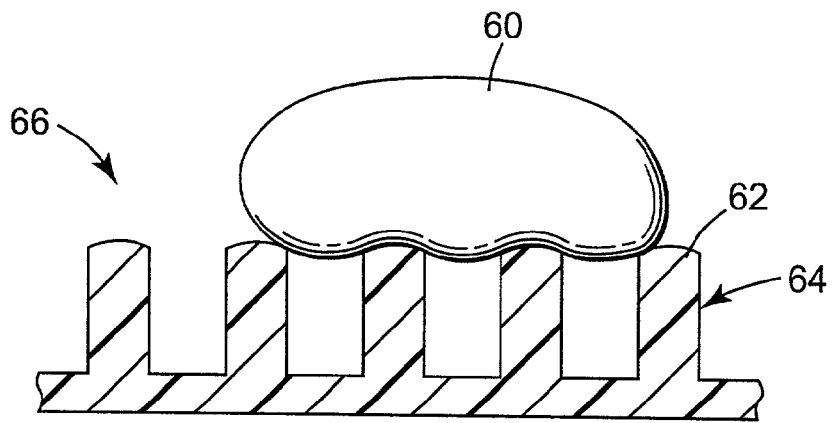
FIG. 6 is a schematic illustration of a water droplet interacting with a slip control article in accordance with the present invention.

A number of mechanisms combine to give the present slip control article exceptional frictional properties in both wet and dry conditions. FIG. 6 is a schematic illustration of an individual water or liquid drop 60 residing on hydrophobic tips 62 of the stems 64. The drop 60 is easily removed from the stem 64 by shaking or gripping of the slip control article 66. The redistribution of liquid (water or other liquid material, including blood, other bodily fluids, and irrigation fluids) can also be impacted by stem density.

Figure 7:
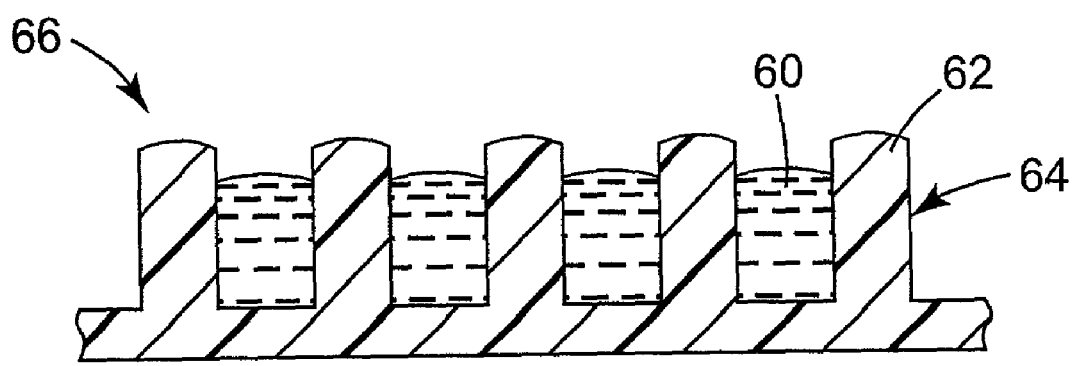
FIG. 7 is a schematic illustration of water being channeled away from the upstanding stems on a slip control article in accordance with the present invention.

Deposition of large amounts of liquid 60 results in distribution of the liquid at the base of the stems 64 while the tips 62 remain dry, as illustrated in FIG. 7. When water or any other polar liquid is deposited on the surface of the slip control article 66, the tips 62 of the stems 64 remain exposed due to the hydrophobic nature of the thermoplastic elastomer polymer. This may prove particularly useful in medical applications, such as when the friction control article is used as a medical drape. In such applications, liquids are distributed across the stems when surgical instruments or other equipment are placed on the drape and the ability of the drape to grip or hold the instruments is preserved. Constructing the backing or base layer from a hydrophilic material assists in directing the fluid 60 away from the tips 62.

The generally upstanding stems 64 grip with other surfaces primarily due to the frictional properties of the elastomeric material of the stems. Frictional performance does not require the stems 64 to protrude into the other surface (i.e., interlocking mechanical engagement is not required like on a two-part mechanical fastener). Therefore, frictional contact can be made with both soft and rigid materials.

The invention relates to a stem web construction with high friction characteristics that are useful in a variety of healthcare applications. The constructions provide gripping properties and are conformable, have a soft feel or touch, and resist linting. The inventive structure comprises a multiplicity of stems arranged in a square, universally spaced or randomly spaced array. When water (or another polar liquid) is applied to the stem web surface of the inventive friction control article, the liquid may distribute into the stemmed surface, between the stems. If the stems have a hydrophobic outer surface, the outermost tips of the stem remain dry due to the hydrophobicity (i.e., low surface energy) of the material they are made of. Tapered walls (optional) on the stems may create additional capillary force that drives fluid from the outermost tips down towards the backing upon which the stems are mounted and project therefrom. This unique interaction with water (or other polar fluids) makes the inventive structure useful for gripping applications.

Soft feel and conformability of the inventive friction control articles can be created by a combination of a soft material, stem geometry and stem spacing. Thus, the positioning of the stems closer to each other than tactile points in human fingers makes it difficult to distinguish individual stems by feel. If present, the reinforcing web or scrim material can also affect the conformability of the composite article. The stems can be made to bend under an applied pressure, which can lend additional softness to the structure where desired. It may also an important feature that the stems be made of a soft, low durometer (e.g., less than 50 Shore D) material which has a high coefficient of friction (e.g., higher than 0.8). In the main, the "softness" component of the construction ostensibly originates from stem bending, rather than from material compression. The stems preferably are therefore formed from a highly resilient elastomeric polymer which has very low values of tension and compression set. As a result, the inventive stem web construction retains a soft tactile feel after multiple uses. Bent stems expose additional surface area available for friction, thus enhancing gripping performance. As the gripping pressure or load is released, the stems will return to their original, generally upwardly projecting positions.

The friction or slip control article provides high shear forces when engaged with another friction or slip control article, at minimal pressure. Since the stems are constructed substantially from a highly flexible elastomeric material, high shear forces are not derived from a mechanical interlock of the stems (such as on a mechanical fastener) or from a mere mechanical blocking from opposed rigid stems. Rather, the frictional properties of the stems are enhanced by the stem size, stem density, and stem pattern when two slip control articles are engaged with each other. The soft, high friction stems of the inventive slip control article are bendable to achieve the desireable characteristics. Possible applications include gloves having the present slip control article located for gripping a surface also including the slip control article. This effect can also be observed when the article is brought in contact with another surface or object, such as with a nonwoven drape, surgical sponge, or other instrument.

When the stem web surfaces of two inventive friction control articles are combined face-to-face, a predetermined blend of mechanical interference and stem to stem friction between the opposed stems create a predictable and reliable friction control interface. While such opposed stem webs may be identical, the stem web surfaces do not have to be identical in nature, material or stem spacing for this to occur. Thus, a 3,000 stem/in$^2$ (465 stem/cm$^2$) pattern on one surface would achieve an effective mechanical interference with a 1,000, 2,000, 3,000, etc., stems/in$^2$ (155, 310 and 465 stems/cm$^2$) pattern on an opposed surface. The shear performance is dependent upon the stem density and is predictable. As a lateral displacement force is applied between the two opposed stem web surfaces, the stems of each surface slip along the sides of the stems of the other surface and may bend. This type of interaction creates a controlled friction force that results from stem engagement which is not at all the same as the interlocking of opposed stems like on a mechanical two-part fastener. The effective coefficient of friction between the two friction control articles depends upon the relative materials used, stem geometries, stem spacings and the magnitude of applied force normal to the friction surface.

Figure 10:
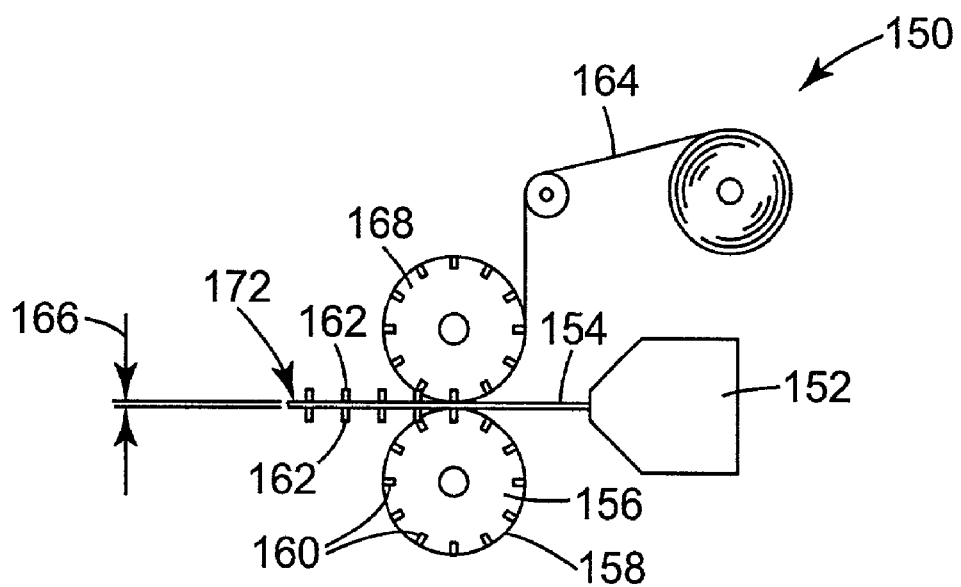
FIG. 10 is a schematic illustration of another exemplary method of manufacturing the slip control article in accordance with the present invention.
Figure 11:
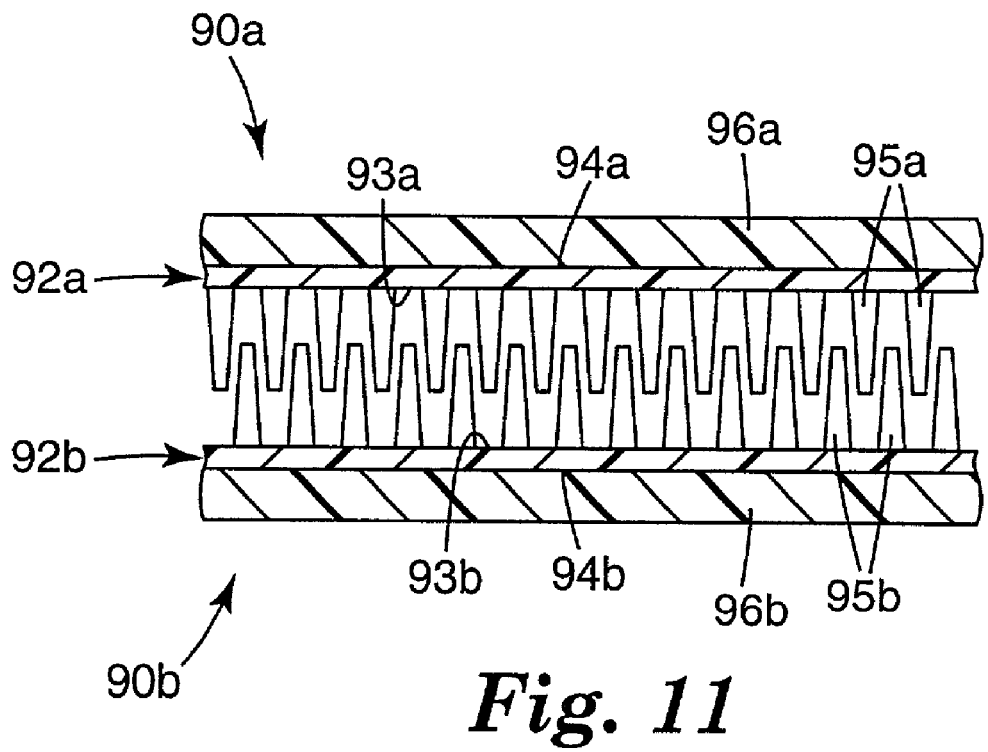
FIG. 11 is a side sectional view of two of the inventive friction control articles in mated contact, such as between a glove and handle where each has the inventive article affixed thereon.
Figure 12:
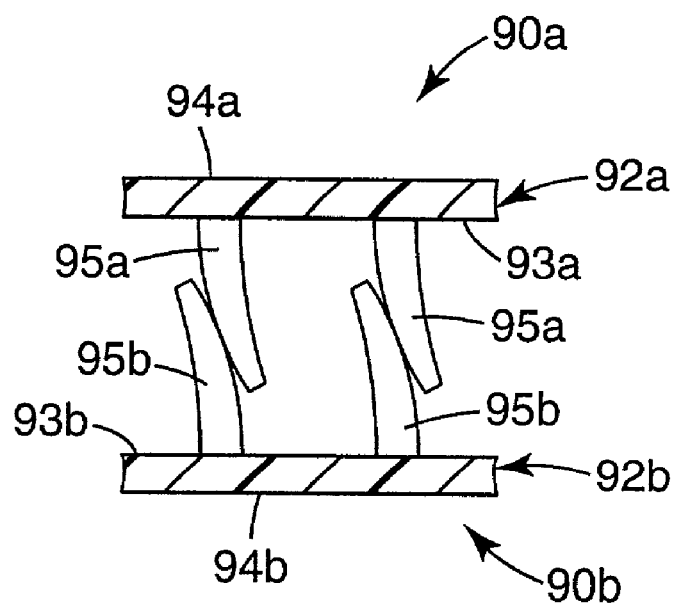
FIG. 12 is an enlarged view of a portion of area A in FIG. 10 as the opposed surfaces move past each other, overcoming stem interference.

FIGS. 10 and 11 illustrate in general terms the relationship between opposed mated stem webs of two friction control articles which are aligned in a face-to-face interference relation. FIG. 10 illustrates opposed slip control articles 90a and 90b. Slip control article 90a has a backing layer 92a with a first surface 93a and a second surface 94a. Stems 95a project from the first surface 93a of the backing layer 92a. Another backing layer or other support body structure 96a is affixed to the second surface 94a of the backing layer 92a. Likewise, the slip control article 90b has a backing layer 92b with a first surface 93b and a second surface 94b. An array of stems 95b projects from the first surface 93b of the backing layer 92b. Another backing layer or other support body structure 96b is affixed to the second surface 94b of the backing layer 92b. When the slip control articles 90a and 90b are aligned in stem web facing alignment (as in FIG. 10) and urged together by a force normal to the stem web arrays thereon, the stems mechanically interfere as shown.

FIG. 11 illustrates in greater detail the contact engagement of opposed stems 95a and 95b when a lateral displacement force is applied between the two opposed slip control articles 90a and 90b. The engaged stems bend yet resist relative lateral movement of the opposed slip control articles 90a and 90b, thus achieving a high shear force resistance, while still providing little or no peel force resistance for separating the opposed slip control articles 90a and 90b. The degree of stem bending depends on material properties, applied forces and the orientation of the stems themselves.

In optimizing the frictional interface of two opposed inventive friction control articles, it is preferred that the total stem area of each friction control article (the area of the stems relative to the total area of the article, as considered in the orientation of FIG. 5B) be less than about 45% to allow for the stems of the two opposed friction control article surfaces to easily fit together. While a less than about 45% total stem area is preferable, a more preferable total stem area is less than about 40%, and an even more preferable total stem area is less than about 35%. In one preferred embodiment, the total stem area is about 30%. There is thus significant void area between the stems in relation to the total stem area. When two of the inventive friction control stemmed surfaces are brought in contact with each other (e.g., FIG. 10), the spacial interference of the stems resists relative lateral movement. Further lateral movement force against one or both of the friction control articles causes the stems to bend and slide against each other (see, e.g., FIG. 11). Resistance to sliding of one friction control gripping surface against the other originates from two factors: (1) the force required to bend the stems to clear the passage, and (2) friction between the walls of the opposed stems. Each factor can be adjusted to address a specific friction control application and achieve desired frictional characteristics. Thus, changing the coefficient of friction of the material forming the stems increases the friction factor. Changing the shapes of the stems, for example making them square in cross section, increases overlap between the stems and will result in higher forces required to bend the stems. A higher flex modulus of the material will bring a similar result, which is a larger magnitude of forces required to slide the opposed surfaces.

In some embodiments, the opposed mating surfaces of the friction control materials may be formed from the same material, with both stems bending in a like manner, or one of the friction control articles may be formed from a material which is stiffer and less flexible than the other (or even rigid). As mentioned above, these factors may be varied to control the desired frictional characteristics of mated friction control articles, so long as one of the arrays of stems is sufficiently flexible to bend to some degree. Generally, the coefficient of friction is a property of the surface and is force independent. In our invention, however, stems deform under the applied vertical load, which alters the effective (measured) coefficient of friction. This later fact makes friction load dependent. Therefore, we introduce the term pseudo-coefficient of friction, which stands for measured coefficient. This later value can be expressed as a ratio of lateral force to the normal force exerted on the article.

The frictional interface between the facing contact surfaces of opposed friction control articles can be predetermined by design, dependent upon the relative materials used, stem geometries, stem spacings and the magnitude of applied force normal to the friction surface. The stems of the opposed stem arrays are aligned in an opposed, contacting and interfitting relation (such as seen in FIG. 10) when a normal force is applied, and the application of a relative lateral displacement force between the stem arrays causes the stems of at least one of the arrays to bend. Relative lateral movement of the two opposed friction control articles is resisted by a predictable force required to bend those stems and the frictional interference between opposed contacting stems.

In a preferred embodiment, a medical or surgical high friction drape is constructed from a dual-sided friction control article. When used in medical or surgical applications, such drapes can be used to drape patients and/or to hold surgical instruments. Such drapes can be placed onto a variety of surfaces, including fabrics such as nonwoven drapes, and resist movement without the aid of adhesives. A further advantage of this embodiment is that such drapes are easily repositionable, do not require an adhesive and release liner, and can be easily sterilized.

The friction control articles may also be fashioned into an article that can be placed directly onto a sterile field during surgery. In such an application, the friction control article (presumably sterilized) is removably attached to the sterile surgical drape it contacts. The top of surface of the friction control article can serve as an instrument holding pad, preventing surgical instruments from sliding off of the sterile field. The bottom surface of the friction control article grips the surface on which it is placed through frictional forces. The article may also be removed and re-placed with ease.

Referring again to FIG. 1, stems that are generally upstanding tend to optimize the performance of the slip control article. The stems are kept upstanding by the stem diameter and the nature of the elastomeric material. The stems typically have a height 28 in the range of about 0.2 mm to about 3 mm, preferably about 0.2 mm to about 1.5 mm. The separation or gap 30 between adjacent stems 26 is generally in the range of about 0.25 mm and about 2.5 mm and more typically in the range of about 0.4 mm to about 1.0 mm. The stems 26 have a maximum cross sectional dimension 29 of about 0.076 mm to about 0.76 mm. The stems 26 are arranged on the backing in a density of at least 15.5 per centimeter squared (100 per square inch), and more typically at least 50 per centimeter squared. The stem density is generally at most about 1500 per centimeter squared, more typically at most about 500 per centimeter squared.

The stems have an aspect ratio of at least 1.25, and preferably at least 1.5, and most preferably at least 2.0. Aspect ratio refers to the ratio of stem height to the maximum cross sectional dimension. For stems with a circular cross section, the maximum cross sectional dimension is the stem diameter. When the stems or pins are formed from an elastomeric material, the relatively small stem diameter enhances the soft nature of the stem web surface to the touch.

Figure 8:
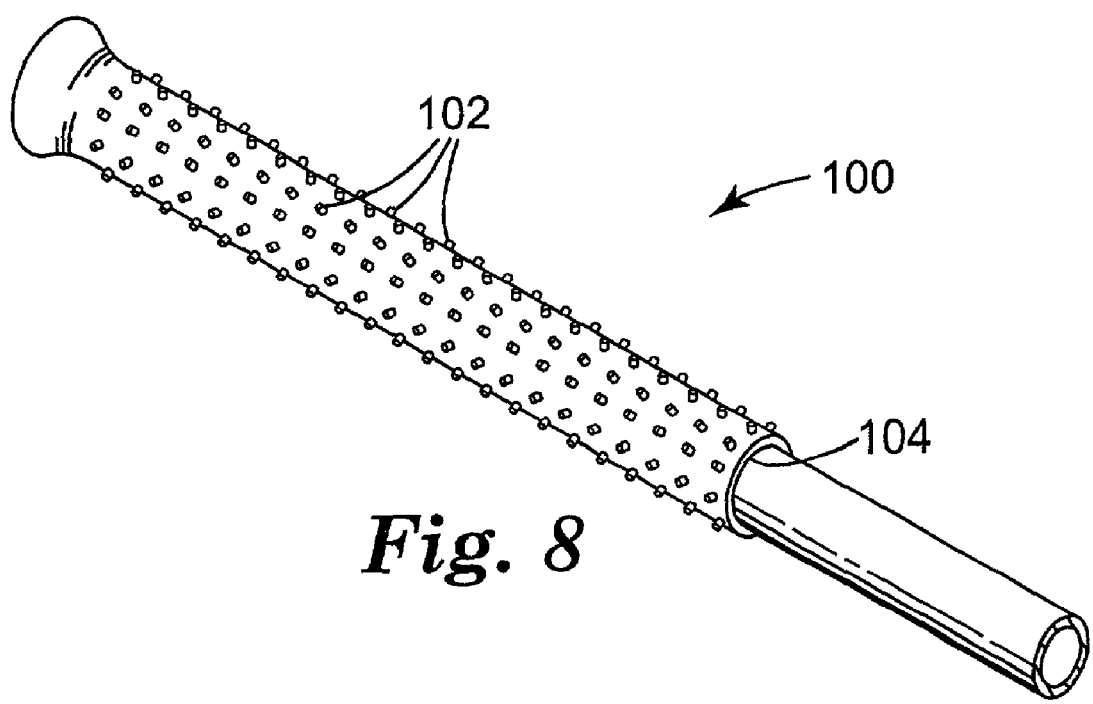
FIG. 8 is a perspective view of an exemplary article incorporating the slip control article of the present invention.

FIG. 8 is a perspective view of an exemplary article 100 incorporating the slip control surface 102 in accordance with the present invention. The article 100 is a grip having an opening 104 at one end, suitable for attachment to a variety of structures such as a surgical instrument. The article 100 may be made using a variety of processes, such as injection molding, profile extrusion, roll extrusion forming, etc.

In some embodiments, providing optical effects on the friction control article may be desired. This may be achieved through additional microreplication techniques on one or both sides of the backing layer and/or by forming the backing layer from a material which is transparent, translucent, polarizing, etc. For example, in reference to the slip control article 20 of FIG. 1, a transparent backing layer 21 would allow printing on the second surface 25 of the backing layer 21 to be visible from the stem web side of the slip control article 20. The stems 26 may also be transparent, or formed from an alternative opaque material or coated with an opaque coating to achieve a variety of desired optical effects. Alternatively, the printing may be applied on the first surface 24 of the slip control article 20 (on the lands between stems 26) for any desired informative, decorative or advertising purpose. A particular slip control article may be fully transparent, or only transparent in part or parts, as desired. For medical or surgical drapes it is generally preferable to color the drapes and/or to reduce or eliminate glare.

In the medial area, numerous uses are also available for the inventive friction control article, used either in a single application or in a mated application. These include:

- on a drape mat to keep tools from sliding during medical procedures
- on seating or reclining areas, such as on dental chairs, examination table surfaces, steps, chiropractic table covers, etc.
- on wheelchair seat, cushion and traction surfaces
- on user and/or floor engaging surfaces of crutches and walkers
- as disposable, attachable surfaces for dental and medical tool handles, and on dental and medical tool trays and mats, including as surgical tool, sterilization and phlebotomy trays
- for dental applications as a patient bib useful as a combined bib and instrument-placing surface as replaceable handle covers for orthopedic and other surgical tools, and/or on operator or surgeon gloves for use thereof as a frictional surface to hold wraps of other materials in place as a material to facilitate the opening of medical containers, including easy open prescription bottles on surfaces within an ambulance or other medical emergency vehicle (e.g., medivac helicopter) to prevent slipping therein, and for enhancing grip of users and/or non-slip surfaces for articles transported thereby as floor mats in medical facilities on medical booties or aseptic shoe covers (inner and/or outer surfaces thereof)

on disposable hospital room or shower mats or pads as shoe inserts to aid in wound care and enhance wearer comfort as pads or patches for nursing home beds to improve air circulation as disposable frictional mats for use in high fluids surgeries (e.g., arthroscopy, urology, etc.)

to secure tubes and cables, including to secure catheters inserted into patients In many of these medical applications, a single friction control article may be sufficient to provide the desired frictional and/or gripping characteristics. Like the other field of use applications mentioned above, high shear strength between opposed mated friction control articles may be achieved by using two friction control articles on opposed surfaces (such as between tool handles and gloves, or between tool handles and holding trays). In addition, the friction control article can be applied to such medical items by either molding it in a particular shape, applying patches thereof using adhesive or other affixing means, or by wrapping the items (such as surgical tools handles) with a tape of the friction control article.

Elastomeric Materials

The elastomeric material can be any thermoplastic elastomer that can be heated to a state in which it can be flowed and molded, such as those described in G. Holden et al., *Thermoplastic Elastomers*, ($2^{nd}$ ed. 1996). It is also within the scope of this invention to use two or more different thermoplastic elastomeric materials in either layered or blended form to define that portion of the slip control article.

The term "elastomer" or "elastomeric" is used to refer to rubbers or polymers that have resiliency properties similar to those of rubber. In particular, the term elastomer reflects the property of the material that it can undergo a substantial elongation and then return to its original dimensions upon release of the stress elongating the elastomer. In all cases an elastomer must be able to undergo at least 10% elongation (at a thickness of 0.5 mm), and more preferably at least 30% elongation, and return to at least 50% recovery after being held at that elongation for 2 seconds and after being allowed 1 minute relaxation time. More typically, an elastomer can undergo 25% elongation without exceeding its elastic limit. In some cases elastomers can undergo elongation to as much as 300% or more of their original dimensions without tearing or exceeding the elastic limit of the composition. Elastomers are typically defined to reflect this elasticity as in ASTM Designation D883-96 as a macromolecular material that at room temperature returns rapidly to approximately its initial dimensions and shape after substantial deformation by a weak stress and release of the stress. ASTM Designation D412-98A can be an appropriate procedure for testing rubber properties in tension to evaluate elastomeric properties.

For some applications, thermoset elastomers may be used. Generally, such compositions include relatively high molecular weight compounds which, upon curing, form an integrated network or structure. The curing may be by a variety of methods, including chemical curing agents, catalysts, and/or irradiation.

The final physical properties of the material are a function of a variety of factors, most notably: number and weight average polymer molecular weights; the melting or softening point of the reinforcing domains (hard segment) of the elastomer (which, for example, can be determined according to ASTM Designation D1238-86); the percent by weight of the elastomer composition which comprises the hard segment domains; the structure of the toughening or soft segment (low $T_g$) portion of the elastomer composition; the cross-link density (average molecular weight between crosslinks); and the nature and levels of additives or adjuvants, etc.

Examples of classes of elastomers include anionic triblock copolymers, polyolefin-based thermoplastic elastomers, thermoplastic elastomers based on halogen-containing polyolefins, thermoplastic elastomers based on dynamically vulcanized elastomer-thermoplastic blends, thermoplastic polyether ester or polyester based elastomers, thermoplastic elastomers based on polyamides or polyimides, ionomeric thermoplastic elastomers, hydrogenated block copolymers in thermoplastic elastomer interpenetrating polymer networks, thermoplastic elastomers by carbocationic polymerization, polymer blends containing styrene/hydrogenated butadiene block copolymers, and polyacrylate-based thermoplastic elastomers. Some specific examples of elastomers are natural rubber, butyl rubber, EPDM rubber, silicone rubber such as polydimethyl siloxane, polyisoprene, polybutadiene, polyurethane, ethylene/propylene/diene terpolymer elastomers, chloroprene rubber, styrene-butadiene copolymers (random or block), styrene-isoprene copolymers (random or block), acrylonitrile-butadiene copolymers, mixtures thereof and copolymers thereof. The block copolymers may be linear, radial or star configurations and may be diblock (AB) or triblock (ABA) copolymers or mixtures thereof. Blends of these elastomers with each other or with modifying non-elastomers are also contemplated. Commercially available elastomers include block polymers (e.g., polystyrene materials with elastomeric segments), available from KRATON Polymers Company of Houston, Tex., under the designation KRATON™.

The elastomeric resin materials, such as those described above, may also have added to them any of a number of customary additives, including, for example, plasticizers, tackifiers, fillers, antioxidants, UV absorbers, hindered amine light stabilizers (HALS), dyes or pigments, opacifying agents and the like. For medical or healthcare applications where the friction control articles are sterilized, it may be particularly advantageous to add one or both of an antioxidant and a HALS.

Antioxidants are desirable for medical articles that may be sterilized by gamma or electron bean radiation. These methods of sterilization, however, generate free radical species that can contribute to rapid degradation of the resin system. It can be particularly useful to choose an antioxidant or a blend of antioxidants that are soluble in the elastomeric resin and that melt during the extrusion process. In this way, the antioxidant becomes uniformly incorporated into the elastomer. Among the useful antioxidants are hindered phonols with hydrophobic chains, such as Irganox™ 1076 available from CIBA Specialty Chemicals of Tarrytown, N.Y. Also useful are multifunctional antioxidants that may incorporate hindered phenols along with oxidizable amine groups. Such antioxidants are commercially available, for example, as Irganox™ 565, also available from CIBA Specialty Chemicals. Irganox 565 also includes alkyl chains (octyl groups) that promote solubility in polymeric resins such as styrene-isoprene di- and triblock copolymers. Irganox 565 used in a concentration of about 0.5 weight percent, is one useful formulation that inhibits degradation normally observed by sterilizing Kraton 1117P by gamma radiation at gamma exposure levels of 25-50 kGy. Other suitable antioxidants are also sold under the "Irganox" trade name by CIBA Specialty Chemicals, including Irganox™ 1010.

Method of Manufacture

Figure 9:
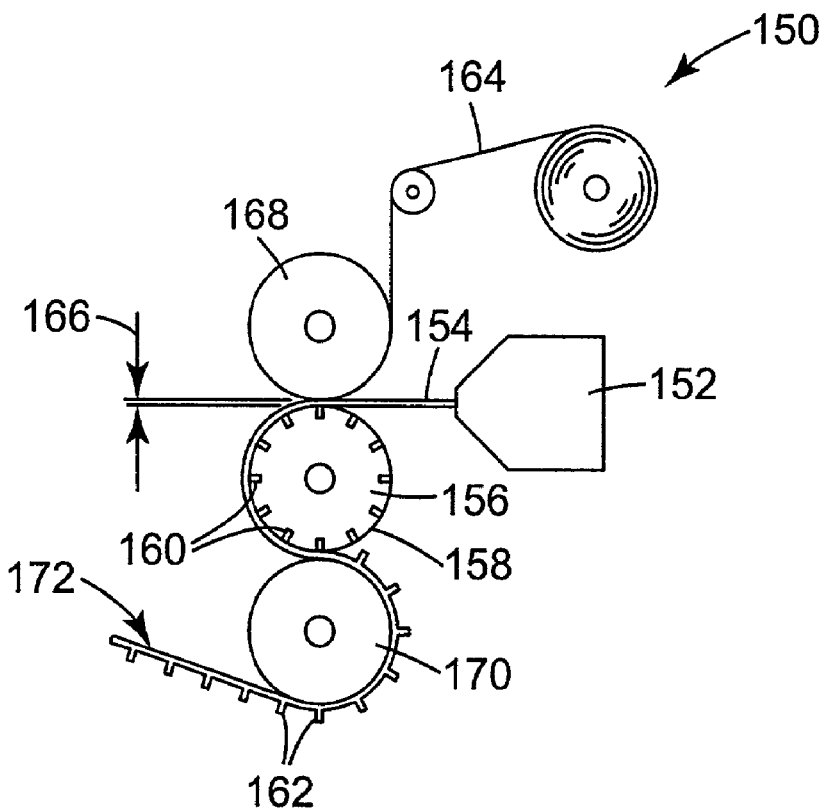
FIG. 9 is a schematic illustration of an exemplary method of manufacturing the slip control article in accordance with the present invention.

The process illustrated in FIG. 9 shows a three-roll vertical stack molding apparatus 150 which includes an extruder and extrusion die 152 adapted for extruding one or more layers of molten thermoplastic material 154 into a mold 156. In this case, the mold 156 is a roll 158, which has on its outer cylindrical surface a desired surface pattern for transference to the molten thermoplastic material 154 as it passes over the cylindrical surface of the roll 158. In the illustrated embodiment, the surface of the roll 158 has a plurality of arranged cavities 160 adapted to form a like plurality of upstanding stems 162. The cavities may be arranged, sized and shaped as required to form a suitable surface stem structures from the thermoplastic material 154. In one embodiment, a sufficient additional quantity of molten thermoplastic material 154 is extruded into the mold 156 to form a portion of the backing layer (see FIGS. 1 and 3).

The roll 158 is rotatable and forms a nip 166, along with an opposed roll 168. The nip 166 between the roll 158 and opposed roll 168 assists in forcing the flow of molten thermoplastic material 154 into the cavities 160 and provides a uniform backing layer thereon. The spacing of the gap forming the nip 166 can be adjusted to assist the formation of a predetermined thickness of the backing layer of thermoplastic material 154. Optionally, backing layer 164 is simultaneously brought into the nip 166. Depending upon the composition of the elastomeric material and the geometry of the upstanding stems 162, the backing layer 164 may be useful in efficiently removing the slip control article 172 from the mold 156.

As illustrated in FIG. 9, the slip control article 172 may traverse a third roll 170 after exiting the roll 158. In this process, the temperatures of all three rolls 158, 168, 170 may be selectively controlled to achieve desired cooling of the thermoplastic material 154. The third roll 170 also serves to define the further path traversed by the slip control article 172.

The mold 158 may be of the type used for either continuous processing (such as a tape, a cylindrical drum or a belt), or batch processing (such as an injection mold or a compression mold). When making a mold 158 for forming the upstanding stems 162, the cavities 160 of the mold 158 may be formed in any suitable manner, such as by drilling, machining, laser drilling, water jet machining, casting, etching, die punching, diamond turning, engraving, knurling and the like. The placement of the cavities determines the spacing and orientation of the slip control article. The stems 162 typically have shapes corresponding to the shape of the cavities 160. The mold cavities can be open at the end of the cavity opposite the surface from which the molten thermoplastic material is applied to facilitate injection of the thermoplastic material into the cavity. If the cavity is closed, a vacuum can be applied to the cavity so that the molten thermoplastic material fills substantially the entire cavity. Alternatively, closed cavities can be longer than the lengths of the stem structures being formed so that the injected material can compress the air in the cavities. The mold cavities should be designed to facilitate release of the surface stem structures therefrom, and thus may include angled side walls, or a release coating (such as a Teflon material layer) on the cavity walls. The mold surface may also include a release coating thereon to facilitate release of the thermoplastic material backing layer from the mold. In some embodiments, the cavities can be angled relative to the surface of the roll.

The mold can be made from suitable materials that are rigid or flexible. The mold components can be made of metal, steel, ceramic, polymeric materials (including both thermosetting and thermoplastic polymers such as silicone rubber) or combinations thereof. The materials forming the mold must have sufficient integrity and durability to withstand the thermal energy associated with the particular flowable thermoplastic material used to form the backing layer and surface topographies. In addition, the material forming the mold preferably allows the cavities to be formed by various methods, is inexpensive, has a long service life, consistently produces material of acceptable quality, and allows for variations in processing parameters.

The molten thermoplastic material is flowed into the mold cavity, and over the surface of the mold to form the layer of cover material. To facilitate flow of the molten thermoplastic material, the thermoplastic material typically must be heated to an appropriate temperature, and then coated into the cavities. This coating technique can be any conventional technique, such as calendar coating, cast coating, curtain coating, die coating, extrusion, gravure coating, knife coating, spray coating or the like. In FIG. 9, a single extruder and extrusion die arrangement is shown. However, the use of two (or more) extruders and associated dies allows simultaneous extrusion into the nip 166 of a plurality of thermoplastic materials to achieve a multi-component (layered or blended) laminate cover material.

The flow of the molten thermoplastic material 154 into the mold 158 may also be facilitated by the application of pressure between opposing rolls 158 and 168. When the backing layer 164 includes a porous material, the three-roll vertical molding apparatus 150 controls the degree of penetration of the molten thermoplastic material 154. In this fashion, the quantity of molten thermoplastic material 154 can be controlled to barely penetrate the surface coating of the backing layer 164, or to penetrate the porous backing layer 164 on the opposite side of introduction of thermoplastic material 154 so as to almost encapsulate the backing layer 164. The penetration of the molten thermoplastic material 154 into the porous backing layer 164 may also be controlled by the temperature of the molten thermoplastic material 154, the quantity of thermoplastic material 154 in the nip 166, and/or by extruder flow rates in conjunction with the line speed of the mold cavities.

After the molten thermoplastic material 154 has been coated into the mold cavities 160 and over the mold surface 156, the thermoplastic material is cooled to solidify and form the desired exterior surface topography thereon (e.g., upstanding stems 162). The solidified thermoplastic material is then separated from the mold 158. The thermoplastic material 154 will often shrink when it is solidified, which facilitates release of the material (e.g., surface stem structures and backing layer) and integral film layer from the mold (see FIG. 1). Part or all of the mold may be cooled to aid in solidifying the surface stem structures and backing layer. Cooling can be effected by the use of water, forced air, heat transfer liquids or other cooling processes.

Some molding processes, such as injection molding, may utilize thermoset elastomeric polymers. When thermosetting resins are used as the molten material, the resin is applied to the mold as a liquid in an uncured or unpolymerized state. After the resin has been coated onto the mold, it is polymerized or cured until the resin is solid. Generally, the polymerization process involves either a setting time, or exposure to an energy source, or both, to facilitate the polymerization. The energy source, if provided, can be heat or radiation energy such as an electron beam, ultraviolet light or visible light. After the resin is solidified, it is removed from the mold. In some instances, it may be desired to further polymerize or cure the thermosetting resin after the surface stem structures are removed from the mold. Examples of suitable thermosetting resins include melamine, formaldehyde resins, acrylate resins, epoxy resins, urethane resins and the like. The formation of a backing layer having upstanding stem structures on at least one side thereof can be performed by injection molding or profile extrusion, such as is disclosed in U.S. Pat. Nos. 4,290,174 (Kalleberg); 5,077,870 (Melbye et al.); and 5,201,101 (Rouser et al.).

One method for making a dual sided friction control article is illustrated in FIG. 10. The process is similar to that depicted in FIG. 9, except that both roll 158 and 168 contain cavities into which the stems are molded. In the process shown in FIG. 10 molten thermoplastic material 154 is extruded from die 152 and passes with optional backing material 164 (e.g., a reinforcing web or scrim material) between rollers 158 and 168 to form dual-sided stemmed web 172, from which the friction control articles may be made.

Test Procedure for Measuring Static and Dynamic Coefficients of Friction

The static and dynamic coefficient of friction for each film sample was measured on a Thwing-Albert Model 225-1 Friction/Peel Tester available from Thwing-Albert Instrument Company, Philadelphia, Pa. Equipment operation is specified in the Thwing-Albert Instruction Manual, Friction/Peel Tester, Model #225-1 revised May 1994, Software version 2.4. This analysis for the static coefficient of friction measured the horizontal force required to cause movement of a weighted 5.08 cm by 5.08 cm (2 inch by 2 inch) sample of the slip control article against a sample of artificial leather sold under the name Ultrasuede™ HP available from Toray Ultrasuede America located in Manhattan, N.Y.

The friction test specimen were prepared by anchoring a 5.08 cm by 5.08 cm (2 inch by 2 inch) sample of the slip control article to a 5.08 cm by 5.08 cm (2 inch by 2 inch) metal test sled. The test specimen were attached to the sled with a two sided pressure sensitive adhesive such as SCOTCH 9851, available from Minnesota Mining and Manufacturing Company, St. Paul, Minnesota. The metal test sled weighed 200 grams.

To prepare the artificial leather sample for the friction test a sample approximately 10.16 cm by 30.48 cm (4 inches by 12 inches) was anchored to a metal sheet with a two sided pressure sensitive adhesive tape, such as SCOTCH 9851 to prevent movement and wrinkling of the sample during the test.

The metal sheet with the sample adhered was clamped on to the metal platen testing surface with the provided spring clip. The metal test sled with film sample on bottom of the sled weighing 200 grams in total was placed on the fabric and pulled for 10 seconds at a speed of 5.1 cm (2 inches) per minute across the fabric per instructions specified in the instructions manual. The static coefficient of friction was then calculated by the machine wherein the measured horizontal force to cause slippage on the sample was divided by the 200 gram normal force of the sled. At least five measurements were recorded for each friction test sample and slip control article. Arithmetic averages were calculated by the friction/peel tester.

Test Method for Dynamic Shear Strength

The dynamic shear strength was measured on an I-mass peel tester. The tester was set up in the 180° Peel Mode. A sample about 3.8 cm×12.7 cm (1.5 inches×5 inches) of stem web was attached using a double sided tape, such as 3 M 404, and centered lengthwise to an about 1.6 mm (1/16 inch) thick, 6.35 cm×22.9 cm (2.5 inches wide×9 inches long) aluminum test panel. Similarly, a sample about 2.54 cm×2.54 cm (1 inch×1 inch) of stem web was attached to the center of an about 1.6 mm (1/16 inch) thick, 6.35 cm×22.9 cm (2.5 inches wide×9 inches long) aluminum test panel. The panels were then placed together with the stems of each sample in contact with each other. The engaged thickness of the two samples without any pressure applied including the aluminum panels was measure using a digital caliper gauge. The weight of the upper panel was approximately 53 grams.

An aluminum panel with the larger sample of stem web was attached to the moving platform of the I-mass tester with the stem web side up. The aluminum panel with the sample about 2.54 cm×2.54 cm (1 inch×1 inch) of stem web was placed on top so that the stem webs were in an engaged position. The stem web was positioned so that it was at the end farthest away from the force gauge so that the sample on the upper panel would be pulled through the lower sample. A bar was placed over the engaged pair with a gap approximately 0.13 mm-0.254 mm (0.005-0.010 inches) greater than the engaged thickness. This bar is designed to prevent the samples from disengaging without exerting undue pressure to engage the two stem web samples. The end of the upper aluminum panel was attached to the force gauge in a position so that the gauge would measure a force directly parallel to the moving platform.

The I-mass tester was balanced, zeroed and adjusted to measure a 2 second averaging time. The position of the spacing bar was adjusted so that it would be directly above the stem web sample during the 2 second averaging time. The platform rate was set at 30.5 cm/minute (12 inches/minute). The peak, valley, and average forces were measure for each sample. Each sample was tested three times and the average values were calculated.

Materials Used in the Examples

A variety of elastomeric materials were used in the preparation of the samples of the examples. These materials are summarized in Table 1. Some properties of some of the samples are summarized in Table 2.

TABLE 1

| Material | Description |
|---|---|
| ESTANE ™ 58661 | available from B. F. Goodrich, Cleveland, OH |
| ESTANE ™ 58238 | available from B. F. Goodrich, Cleveland, OH |
| VECTOR ™ 4111 | available from Exxon Chemical Co., Houston, TX |
| ESTANE ™ 5740-820 | available from B. F. Goodrich, Cleveland, OH |
| KRATON ™ G1657 | available from Shell Oil Co., Houston, TX |

TABLE 2

| Material | Modulus @ 100%, MPa | Ultimate elongation | Tensile set 200% elongation | Friction Coef. | Tensile strength MPa | Hardness, Shore A |
|---|---|---|---|---|---|---|
| Polyurethane Estane™ 58238 | 4.5 | 680% | 3% | 1.35 | 48.3 | 75 |
| Polyurethane Estane™ 58661 | 5.86 | 640% | 3% | 1.4 | 52.4 | 80 |
| Polyurethane Estane™ 5740x820 | 3.8 | 750% | 5.6% | 1.5 | 24.9 | 79 |
| Vector™ 4111 | 1.9 | 1200% | 15% | 2.55 | 29 | 38 |
| Kraton™ G1657 | 2.4 | 750% | 10% | 2.1 | 23.4 | 65 |
| MPR Alcryn™ 2080-BK | 6.45 | 280% | 8% | .9-2.6 | 13 | 77 |

Rheology and Morphology of the Blends

Viscosities of both Estane™ 58661 and Vector™ 4111 were measured over several decades of shear rate using both a DSR and a capillary rheometer (CR) at 204° C. (400° F.), the temperature used in the stem web extrusion. It is apparent that at higher shear rates (>10 s-1), the viscosity and elasticity modulus of Vector™ 4111 are approximately twice that of Estane™ 58661.

Scanning electron microscopy (SEM) was used to investigate the morphology of blends of various compositions. The blends were mixed using a Brabender mixer and pressed into a silicone mold using a hot press method at about 216° C. (420° F.) at 6.9 MPa (1000 psi) for 60 seconds. The tool containing the material was cooled on dry ice. The sample was peeled from the mold. Only hot-pressed blends, described below, were studied. Micrographs were taken near the sample surface. A dispersed morphology was present in nearly every sample. Only in the 60/40 Estane™ 58661/Vector™ 4111 sample were any co-continuous structures present.

EXAMPLES

Example 1

A 50:50 by weight of polyurethane resin Estane™ 58661 and a styrenic triblock copolymer Vector™ 4111 was dry blended as pellets. Polyurethane provided durability and resiliency of the structure while Vector improved frictional performance. The Estane™ 58661 was dried at about 82.3° C. (180° F.) for at least 4 hours. The mixture of pellets was mixed with about 2 wt % of carbon black/polyurethane blend. The content of carbon black in the final blend did not exceed 1 wt %.

The mixture was extruded as generally illustrated in FIG. 9, except that the tooling was configured as a belt rather than a roll. The extruder as a Davis Standard single screw extruder with about 6.35 cm (2.5 inches) screw diameter designed for polyolefin processing. At about 8 revolutions per minute (rpm), the melt was discharged through the die at melt pressure of about 13.8 MPa (2000 psi). The temperature in the last zone of the extruder was about 216° C. (420° F.). The temperature of the die was about 232° C. (450° F.). The opening of the die lip was about 0.51 millimeters (0.020 inches).

The melt was pressed into a silicone belt/tool with a metal roll at a nip pressure of about 345,705 Pa (50 psi). One of the rolls had a tooled surface that was heated to about 65.6° C. (150° F.). The surface contained an array of holes about 0.254 mm (0.010 inches) in diameter and about 0.46 cm (0.018 inches) apart. A backing layer of double coated tape available from Minnesota Mining and Manufacturing Company under product designation 404 was introduced into the nip and bonded to the side of the web opposite the upstanding stems. The web and double coated tape was removed from the tooled surface at a speed of about 1.5 meters/minute (5 feet per minute).

The resulting stem web had about 490 stems/centimeters$^2$ (3159 stems per square inch). The center-to-center spacing of the stems was about 0.43 9 mm (0.0173 inches) in the x-direction and about 0.465 mm (0.0183 inches) in the y-direction. Stem diameter was about 0.15 mm (0.0059 inches) and the stem height was about 0.625 mm (0.0246 inches). The gap between adjacent stems was about 0.127 mm (0.005 inches).

Wetting capability of water was estimated by measuring a contact angle between a drop of water and flat substrate with the same composition as the stem web. The contact angle was measured to be about 65°, which was expected for a hydrophobic material (see generally FIG. 6). A large amount of water was then applied to the structured surface of the stem web and viewed in optical microscope. Water completely filled the space between the stems. The tips of the stems were exposed due to hydrophobic nature of the elastomer, as shown in FIG. 7. As a result of the exposed tips, frictional properties were improved when compared to flat sheet performance, when tested under the same conditions.

The gripping performance was evaluated using two approaches. The first set of experiments included direct measurements of the frictional properties of the stem web. The results were compared to the performance of the flat substrate made of the same polymer blend as the stem web. The second approach involved direct application of the stem web to an article. A 68.6 cm×2.54 cm (27 inches×1 inch) strip of the web was wrapped around a golf shaft and compared to the existing golf grips performance in both wet and dry conditions. A panel of evaluators took a series of swings with the golf club with the new grip. The performance of the invention was believed to be superior to the control sample in wet conditions. A similar test was conducted with a tennis racket.

Example 2

For more consistent removal of the stem web from the tooled surface and uniform application the articles, a two-layer construction was created using a co-extrusion process.

The tooling and processing parameters were as described in Example 1 unless otherwise specified. Rather than the backing layer of the double coated tape in Example 1, a backing layer made of a 80:20 wt % blend of polyurethane Estane™ 58137 and Vector™ 4111 was co-extruded with the stem web. The polyurethane had hardness of 70 Durometer and the modulus of about 22 MPa (3200 psi). The stiffer backing layer was extruded using about 6.35 cm (2.5 inches) diameter screw at about 5 rpm. The top layer which formed the stemmed portion of the construction was extruded using about a 3.2 cm (1.25 inches) diameter screw extruder operating at about 15 rpm. The temperature profile was the same as described in Example 1. The polymer melt was discharged at a minimum pressure of about 6.9 MPa (1000 psi) and at the temperature in the front zone of about 216° C. (420° F.).

Both melts were combined in Cloeren feed block model no. 86-120-398 at about 232° C. (450° F.). A Cloeren extrusion die with a deckle system, model no. 89-12939, was used. The construction was removed from the tooled surface at about 1.5 meters/minute and about 3 meters/minute (5 fpm and 10 fpm). The resulting thickness of the each layer (not including the stems), at about 5 fpm take-up speed was about 0.254 mm (0.010 inches).

Example 3

A stem web was made generally according to Example 2 using a tool with different stem geometry and a pressure of about 68,941 Pa (10 psi), resulting in shorter stems. The stem web was a 80:20 by weight of polyurethane resin Estane™ 58661 and a styrenic triblock copolymer Vector™ 4111. The backing layer was made of a 80:20 wt % blend of polyurethane Estane™ 58137 and Vector™ 4111, co-extruded with the stem web as in Example 2.

The resulting stem web had about 235 stems/centimeters$_2$ (1516 stems per square inch). The center-to-center spacing of the stems was about 0.676 mm (0.0266 inches) in the x-direction and about 0.630 mm (0.0248 inches) in the y-direction. Stem diameter was about 0.198 mm (0.0078 inches) and the stem height was about 0.307 mm (0.0121 inches). The gap between adjacent stems was about 0.127 mm (0.005 inches).

Example 4

A stem web with a single layer construction and a density of about 139 stems/cm$^2$ (900 stems/square inch) was created using a tool with different stem geometry and the same processing conditions and polymer blend formulation as in Example 1. The stems had about 50% larger diameter than the stems on the about 465 stems/cm$^2$ (3000 stems/square inch) construction of Example 1, which lead to better durability of the construction. Stem height was about 0.56 mm to about 0.61 mm (0.022 inches to 0.024 inches). At a distance between the pins of about 0.84 mm (0.033 inches), individual pins could be felt. Thicker pins are also less flexible, which also contributed to a more rough, or coarse feel of the surface. This surface is most suited for non-skin contact applications.

Example 5

A stem web was made using a tool with different stem geometry and substantially according to Example 1 with a 80:20 by weight of polyurethane resin Estane™58661 and a styrenic triblock copolymer Vector™4111. The resulting stem web had about 46 stems/centimeters$_2$ (299 stems per square inch). The center-to-center spacing of the stems was about 1.68 mm (0.066 inches) in the x-direction and about 1.29 mm (0.0507 inches) in the y-direction. Stem diameter was about 0.459 mm (0.0195 inches) and the stem height was about 0.617 mm (0.0243 inches). The gap between adjacent stems was about 0.254mm (0.010 inches). The higher percentage of polyurethane increased durability of the resulting slip control article.

Example 6

Stem web sheets were made using silicone tooling similar to Example 1 and the hot press method discussed above. The formulations are set forth in Table 3, where the ratios refer to percentage of Estane™58661 to Vector™4111. The resulting stem web had about 490 stems/centimeters$_2$ (3159 stems per square inch). The center-to-center spacing of the stems was about 0.439 mm (0.0173 inches) in the x-direction and about 0.465 mm (0.0183 inches) in the y-direction. Stem diameter was about 0.15 mm (0.0059 inches) and the stem height was about 0.625 mm (0.0246 inches). The gap between adjacent stems was about 0.127 mm (0.005 inches).

In order to quantitatively compare the group properties of various blend compositions in both wet and dry conditions, a Thwing-Alber friction/peel tester was used to measure both static (SFC) and dynamic (DFC) friction. In addition, friction coefficients for flat sheets, i.e. the other side of the stem web, were also measured for a few of the blend compositions. The average SFC and DFC values for stem webs prepared in a batch process using a heated press of various formulations are given in Table 3.

TABLE 3

Frictional properties of blended stem webs in dry and wet conditions.

| Formulation | SFC Dry | DFC Dry | SFC Wet | DFC Wet |
|---|---|---|---|---|
| Estane 58661 | 1.3 | 1.25 | 1.2 | 1.1 |
| 80/20 | 1.5 | 1.5 | 1.4 | 1.4 |
| 60/40 | 1.8 | 1.75 | 1.7 | 1.6 |
| 50/50 | 1.85 | 1.75 | 1.7 | 1.6 |
| 40/60 | 2.1 | 2.0 | 2.0 | 1.9 |
| 20/80 | 2.3 | 2.11 | 2.1 | 1.8 |
| Vector 4111 | 2.5 | 2.3 | 2.3 | 2.1 |

Stem samples made from pure Vector™ 4111 have the highest DFC and SFC, and pure Estane™ 58661 stem samples have the lowest DFC and SFC. Mixtures are somewhere in between with a nearly linear relationship. In addition, SFC and DFC for each blend decreases with the addition of water between the stems and the Ultrasuede™ substrate. In fact, the addition of water causes an only about a 7% decrease in stem web friction for every blend composition. Small differences in friction performance are found for 50/50 and 60/40 blends. Based on frictional performance, the 60/40 formulations will lead to better wear properties since it possess a larger volume fraction of polyurethane.

Example 7

A stem web of 50:50 by weight of polyurethane resin Estane™ 58661 and a styrenic triblock copolymer Vector™ 4111 was made according to Example 1. The stem geometry is as set forth in Example 1. A flat sheet was also made using this formulation. The average SFC and DFC values for stem web and the flat sheet are given in Table 4.

TABLE 4

Stem web and flat film comparison.

| Sample ID | SFC Dry | DFC Dry | SFC Wet | DFC Wet |
|---|---|---|---|---|
| Flat Film | 2.12 | 2.08 | 1.3 | 1.3 |
| Stem web | 2.1 | 2.0 | 2.05 | 1.95 |

From Table 4 it is evident that both static and dynamic coefficients of friction are comparable for the stem web (60% Estane™ 58661 and 40% Vector™ 4111) and flat sheet when measured in dry conditions. However, when some water was added to the stem web, coefficient of friction of the flat sheet decreased by 30%, while stem web maintained its high friction, within the experimental error. This result is consistent with the mechanism of wetting described on FIGS. 6 and 7.

Example 8

Three samples of the stem webs of Examples 1, 3 and 5 were examined for dynamic shear strength using the test method described above. A summary of the results is found in Table 5.

TABLE 5

Dynamic Shear Strength-Dynes/cm$^2$ (ounces/inch$^2$)

| Example | Sample | Peak | Valley | Average |
|---|---|---|---|---|
| 1 | 1 | 168,481 (39.1 oz/sq. in.) | 140,904 (32.7 oz/sq. in.) | 157,709 (36.6 oz/sq. in.) |
| 1 | 2 | 144,351 (33.5 oz/sq. in.) | 140,904 (32.7 oz/sq. in.) | 143,489 (33.3 oz/sq. in.) |
| 1 | 3 | 202,523 (47.0 oz/sq. in.) | 81,009 (18.8 oz/sq. in.) | 136,595 (31.7 oz/sq. in.) |
| 1 | Average | 171,929 (39.9 oz/sq. in.) | 121,082 (28.1 oz/sq. in.) | 146,075 (33.9 oz/sq. in.) |
| 3 | 1 | 18,959 (4.4 oz/sq. in.) | 14,650 (3.4 oz/sq. in.) | 16,805 (3.9 oz/sq. in.) |
| 3 | 2 | 23,268 (5.4 oz/sq. in.) | 18,959 (4.4 oz/sq. in.) | 21,545 (5.0 oz/sq. in.) |
| 3 | 3 | 35,333 (8.2 oz/sq. in.) | 21,114 (4.9 oz/sq. in.) | 31,886 (7.4 oz/sq. in.) |
| 3 | Average | 25,854 (6.0 oz/sq. in.) | 18,097 (4.2 oz/sq. in.) | 23,268 (5.4 oz/sq. in.) |
| 5 | 1 | 168,051 (39.0 oz/sq. in.) | 107,725 (25.0 oz/sq. in.) | 133,148 (30.9 oz/sq. in.) |
| 5 | 2 | 152,969 (35.5 oz/sq. in.) | 80,578 (18.7 oz/sq. in.) | 135,733 (31.5 oz/sq. in.) |
| 5 | 3 | 152,538 (35.4 oz/sq. in.) | 81,009 (18.8 oz/sq. in.) | 112,034 (26.0 oz/sq. in.) |
| 5 | Average | 157,709 (36.6 oz/sq. in.) | 89,627 (20.8 oz/sq. in.) | 127,115 (29.5 oz/sq. in.) |

The stem webs made according to Examples 1 and 5 had the best dynamic shear strength. The samples from Examples 1 and 3 were more similar in stem density and stem meter than those of Example 5. However, the stem height of the samples of Example 3 approximately half the height of the stems of Examples 1 and 5. Even the relatively density stem web of Example 5 outperformed the samples of Example 3. Therefore, stem height appears to be a significant factor in dynamic shear strength.

Example 9

A stem web was made using a tool with different stem geometry and substantially according to Example 1 with a 78:2:20 by weight blend of polyurethane Estane™ 28238, a black colorant (based on Estane™ 58238), and a styrene-isoprene-styrene triblock copolymer Vector™ 4111, respectively. The resulting stem web had about 3,100 stems/inch$^2$, with stem diameters of about 10 mil and stem heights of about 19 mil. The stems were arrayed in a square pattern, with equal spacing between adjacent stems in the x-direction and y-direction. The product specs for a friction control article of this example are a stem density of 2,500-3,500 stems/inch$^2$, a stem diameter of 9-11 mils. and a stem height of 14-24 mils. The friction control article of this example provides a stem web construction with high friction characteristics (the pseudo-coefficient of friction at 100 grams/inch$^2$ load was at least 6) and soft feel to the touch, suitable for such uses as bicycle handlebar grips and mating bicycle gloves. The stems are relatively flexible and bendable which creates the desired and predicted friction relationship between such a glove and grip.

Example 10

A high friction pad useful, for example as a pad to hold surgical instruments with a pattern of stems on the top and bottom surfaces is made by the following process.

Polymeric Composition

Table 6 contains the polymeric composition of stems and base layer of a high friction article.

TABLE 6

Composition of Stems and Base Layer of a High Friction Article

| Amount (wt %) | Generic Name | Trade Name | Source and Address |
|---|---|---|---|
| 98.5 | Linear styrene-isoprene-styrene block copolymer | KRATON D-1117P | KRATON Polymers, Houston, Texas |
| 0.5 | Anti-oxidant | IRGANOX 565 | Ciba Specialty Chemicals Corp., Tarrytown, New York |
| 1.0 | White Pigment | Number 1015100S | Clariant Corporation, Milford, Delaware |

Preparation of Master Tool Mold

A replication master tooling article prepared as described in U.S. Pat. No. 5,792,411 (Morris et al.) with a 140 stems per square centimeter hole pattern was placed on each of two co-rotating rolls.

Process

The polymeric composition was mixed in a single screw Killion extruder (available as Model KTS-125 from Killion Extruders, Inc., Ceadar Grove, N.J.) with L:D ratio of 24:1 and a single layer feed-block which fed into a slot die as described in U.S. Pat. Nos. 4,152,387 (Cloeren) and 4,780,258 (Cloeren). The temperature of the extruder ranged from 199° C. to 215° C. The temperature of the die was maintained at 241° C. The molten polymer mixture was extruded to the junction of two co-rotating rolls at a flow rate of 3 grams per centimeter per minute. The temperature of the rolls was maintained at 54° C. to cool the polymeric composition. The nip pressure between the co-rotating rolls was maintained at 345 KPa (50 pounds per square inch).

A woven polyester scrim (available as Style 490 from American Fiber and Finishing, Inc., Newberry, S.C.) was introduced between the co-rotating rolls. The scrim had a count of 22 by 10 threads per 2.54 centimeters and the threads were 167 dtex (150 denier) with 70 filaments per thread.

The molten polymer composition was extruded simultaneously with the woven scrim such that the polymer composition and the scrim were compressed between the master tools on the co-rotating rolls. The nip pressure provides the force needed to drive the polymer composition through the scrim and into the hole pattern of the master tool. The line speed was maintained at 1.5 meters per minute. As the combination of polymer composition and scrim exit the co-rotating rolls, a two sided polymeric stem structured film is produced. There were 140 stems per centimeter on both sides of the film and the stems were approximately 508 micrometers in height.

This film is useful for a variety of purposes including as a high friction surgical instrument pad which is used to prevent instruments from falling on the floor during surgery.

Example 11

A high friction surgical pad with a pattern of stems on the top surface is made by the following process.

Polymer pellets (linear styrene-isoprene-styrene block copolymers commercially available as KRATON™ D1107P, D1112P, D1117P, D1119P, and D1193X from KRATON Polymers, Houston, Tex. and polyurethane based on polytetramethylene glycol with a Shore A Hardness of 72A commercially available as Pellethane 2103-70A from Dow Chemical, Midland Mich.) were pressed into sheets approximately 0.3 cm thick in a heated platten press at temperatures of 149° C. and a force on a 15.24 cm square platten of 2,268-3,175 kilograms (kg). The pellets were pressed between two sheets of a silicone coated premium release paper release liner.

The polymer sheets were substantially free of large bubble defects. These sheets were allowed to cool and then subsequently pressed into one of two replication master tooling articles prepared as described in U.S. Pat. No. 5,792,411 (Morris et al.) with a 30 holes per square centimeter density and with a 248 holes per square centimeter density by creating a sandwich in the press with one of the replication master tooling articles on the bottom, the polymer in the middle, and a piece of the release liner on the top (printed side against polymer). This was then pressed at a temperature of 143-160° C. and a force of 2,268-3,629 kg. The samples were allowed to dwell at this pressure for at least 15 seconds before the pressure was released. Once cool the stem webs were removed from the mold for testing. The 30 hole/cm$^2$ pattern produced stems with a diameter of 0.35-0.40 mm and a height of 3.2-3.8 mm. The 248 hole/cm$^2$ pattern produced stems with a diameter of approximately 0.2 mm with a height of 0.4-0.6 mm. The samples were tested for the stainless steel kinetic coefficient of friction (the "Stainless Steel Kenetic Coefficient of Friction") wet and dry as described in U.S. Pat. No. 4,667,661 (Scholz et al.) except that the flat side of the sled was against the sample. The sled was pulled at 127 cm/min. The KCOF was taken as the average force integrated over 7.62 cm (3 inches) of pull per 200 g (weight of sled). Wet values were obtained by fully saturating the web with water and repeating the test.

The Stainless Steel Static Coefficient of Friction was taken as the peak value required to get the sled moving. The results are the average of two measurements and are reported in Table 7 for the SCOF and Table 8 for the KCOF.

TABLE 7

Stainless Steel Static Coefficient of Friction (Wet and Dry) for Two Master Tooling Articles with Different Hole Densities

| Run | Polymer | Hole Density (holes/cm$^2$) | Coefficient of Friction Value (g/g) | |
|---|---|---|---|---|
| | | | Dry | Wet |
| 1 | KRATON D1107P | 248 | 2.2 | 2.3 |
| 2 | KRATON D1112P | 248 | 2.8 | 2.5 |
| 3 | KRATON D1117P | 248 | 3.0 | 2.9 |
| 4 | KRATON D1119P | 248 | 2.9 | 2.5 |
| 5 | KRATON D1193X | 248 | 2.1 | 2.3 |
| 6 | Pellethane 2103-70A | 248 | 1.4 | 1.3 |
| 7 | KRATON D1107P | 30 | 2.1 | 2.4 |
| 8 | KRATON D1112P | 30 | 2.8 | 2.3 |
| 9 | KRATON D1117P | 30 | 3.0 | 2.9 |
| 10 | KRATON D1119P | 30 | 2.6 | 2.6 |
| 11 | KRATON D1193X | 30 | 1.5 | 1.8 |
| 12 | Pellethane 2103-70A | 30 | 1.2 | 1.3 |

TABLE 8

Stainless Steel Kinetic Coefficient of Friction (Wet and Dry) for Two Master Tooling Articles with Different Hole Densities

| Run | Polymer | Hole Density (holes/cm$^2$) | Coefficient of Friction Value (g/g) | |
|---|---|---|---|---|
| | | | Dry | Wet |
| 1 | KRATON D1107P | 248 | 2.2 | 2.5 |
| 2 | KRATON D1112P | 248 | 2.8 | 2.3 |
| 3 | KRATON D1117P | 248 | 2.7 | 2.6 |
| 4 | KRATON D1119P | 248 | 2.7 | 2.2 |
| 5 | KRATON D1193X | 248 | 2.3 | 2.3 |
| 6 | Pellethane 2103-70A | 248 | 1.4 | 1.3 |
| 7 | KRATON D1107P | 30 | 2.4 | 2.4 |
| 8 | KRATON D1112P | 30 | 2.8 | 2.6 |
| 9 | KRATON D1117P | 30 | 3.2 | 3.2 |
| 10 | KRATON D1119P | 30 | 3.0 | 3.0 |
| 11 | KRATON D1193X | 30 | 1.7 | 1.9 |
| 12 | Pellethane 2103-70A | 30 | 1.4 | 1.3 |

The data indicates that the KRATON samples had much higher static and kinetic coefficient of friction values than the polyurethane sample tested. The KRATON D1117P had the highest values.

Patents and patent applications disclosed herein are hereby incorporated by reference. Other embodiments of the invention are possible. It is to be understood that the above description is intended to be illustrative, and not restrictive. In these application as well as those disclosed and suggested above, the inventive friction control article can include one or more of the features of the various embodiments disclosed herein, such as having micro-channels along one of the surfaces of the backing layer to aid in quickly dispersing liquids and thus enhancing the desired friction control characteristics of the article when wet. Many other embodiments will be apparent to those of skill in the art upon reviewing the above description. The scope of the invention should, therefore, be determined with reference to the appended claims, along with the full scope of equivalents to which such claims are entitled.

We claim:

1. A medical drape comprising:
   a backing layer having a first surface and a second surface, where projecting from the first surfane of the backing layer is a soft and flexible array of stems which are integrally formed with the backing layer;
   wherein at least a portion of the exterior surface of the stems comprises an elastomeric material selected from the group consisting of anionic triblock copolymers; thermoplastic elastomers based on halogen-containing polyolefins; thermoplastic elastomers based on dynamically vulcanized elastomer-thermoplastic blends; thermoplastic polyether ester and polyester based elastomers; thermoplastic elastomers based on polyanaides or polyimides; jonomeric thermoplastic elastomers; hydrogenated block copolymers in thermoplastic elastomer interpenetrating polymer networks; thermoplastic elastorners made by carbocationic polymerization; polymer blends containing styrene/hydrogenated butadiene block copolymers; polyacrylate-based thermoplastic elastomers; natural rubbers; butyl rubbers; EPDM rubbers; silicone rubbers; polyisoprenes; polybutadienes; polyurethanes; ethylene/propylene/diene terpolymer elastomers; chloroprene rubbers; random and block styrene-butadiene copolymers; random and block styrene-isoprene copolymers; acrylonitrile-butadiene copolymers; and mixtures and copolymers thereof;
   wherein the aspect ratio of the stems on the first surface of the backing layer is at least about 1.25; and
   wherein the drape has a static coefficient of friction when dry along at least a portion of the first surface of at least 0.6.

2. The medical drape of claim 1 wherein the stems are generally upstanding.

3. The medical drape of claim 1 wherein the elastomeric material is thermoplastic.

4. The medical drape of claim 1 wherein the static coefficient of friction when wet is within 20 percent of the static coefficient of friction when dry.

5. The medical drape of claim 1 wherein the static coefficient of friction when wet is Within 80 percent of the static coefficient of friction when dry.

6. The medical drape of claim 1 wherein the static coefficient of friction when wet is Within 90 percent of the static coefficient of friction when dry.

7. The medical drape of claim 1 wherein protruding from the second surface of the backing layer is a second array of stems.

8. The medical drape of claim 1 farther comprising a second backing layer adjacent to the second surface of the first backing layer, where projecting from the second backing layer is a second array of stems.

9. The medical drape of claim 8 wherein at least a portion of the exterior surface of the stems of the second array comprises an elastomeric material.

10. The medical drape of claim 8 farther comprising a reinforcing layer disposed between the first and second backing layers.

11. The medical drape of claim 10 wherein the reinforcing layer is a nonwoven scrim material.

12. The medical drape of claim 10 wherein the reinforcing layer is a woven scrim material.

13. The medical drape of claim 1 further comprising a reinforcing layer adjacent to the second surface of the backing layer.

14. The medical drape of claim 13 wherein the reinforcing layer is a nonwoven scrim material.

15. The medical drape of claim 13 wherein the reinforcing layer is a woven scrim material.

16. The medical drape of claim 13 further comprising a second backing layer adjacent to the reinforcing layer, where projecting from the second backing layer is a second array of stems.

17. The medical drape of claim 16 wherein at least a portion of the exterior surface of the stems of the second array comprises an elastomeric material.

18. The medical drape of claim 1 further comprising micro-channels between the stems along at least a portion of the exterior of the first surface of the backing layer.

19. The medical drape of claim 1 wherein the density of the stems on the first surface of the backing layer is at least 15.5 stems/cm$^2$.

20. The medical drape of claim 1 wherein the elastomeric material further comprises at least one antioxidant.

21. A medical drape comprising:
    a backing layer having a first surface and a second surface, where projecting from the first surface of the backing layer is a soft and flexible array of stems which are integrally formed with the backing layer;
    wherein the aspect ratio of the stems on the first surface of the backing layer is at least about 1.25; and
    wherein the drape has a static coefficient of friction when dry along at least a portion of the first surface of at least 0.6.

22. A medical drape comprising:
    a backing layer having a first surface and a second surface, where projecting from the first surface of the backing layer is a soft and flexible array of 15.5 to 1500 upstanding stems per centimeter squared which are integrally formed with the backing layer;
    wherein at least a portion of the exterior surface of the stems comprises an elastomeric material with a Shore hardness of less than about 90 A;
    wherein the aspect ratio of the stems on the first surface of the backing layer is at least about 1.25;
    wherein each stem has a maximum cross sectional dimension of 0.076 to 0.76 mm; and
    wherein the drape has a static coefficient of friction when dry along at least a portion of the first surface of at least 0.6.

23. The medical drape of claim 22, wherein the elastomeric material has a Shore hardness of less than about 50 A.

24. The medical drape of claim 22, wherein the drape has a dynamic shear strength of at least 112,034 dynes per centimeter squared.

* * * * *

UNITED STATES PATENT AND TRADEMARK OFFICE
CERTIFICATE OF CORRECTION

PATENT NO. : 7,309,519 B2
APPLICATION NO. : 09/982741
DATED : December 18, 2007
INVENTOR(S) : Matthew T. Scholz It is certified that error appears in the above-identified patent and that said Letters Patent is hereby corrected as shown below:

On the Title Page, item [57], in Column 2, under (Abstract)
Line 2, delete "Layer" and insert -- layer --, therefor.

Column 1
Line 4, delete "CROSS REFERENCE" and insert -- CROSS-REFERENCE --, therefor.

Column 2
Line 8, delete "a" and insert -- an --, therefor.

Column 4
Line 66, before "it" delete "the".

Column 6
Line 14, delete "regions" and insert -- region --, therefor.
Line 27, delete "an" and insert -- a --, therefor.

Column 7
Line 58, delete "desireable" and insert -- desirable --, therefor.

Column 8
Line 63, delete "spacial" and insert -- spatial --, therefor.

Column 12
Line 67, delete "phonols" and insert -- phenols --, therefor.

Column 13
Line 7, delete "Irganox 565" and insert -- Irganox$^{TM}$ 565 --, therefor.
Line 9, delete "Irganox 565" and insert -- Irganox$^{TM}$ 565 --, therefor.

Column 16
Line 21, delete "inch )" and insert -- inch) --, therefor.

Column 18
Line 29, delete "0.43 9" and insert -- 0.439 --, therefor.

UNITED STATES PATENT AND TRADEMARK OFFICE
CERTIFICATE OF CORRECTION

PATENT NO. : 7,309,519 B2
APPLICATION NO. : 09/982741
DATED : December 18, 2007
INVENTOR(S) : Matthew T. Scholz It is certified that error appears in the above-identified patent and that said Letters Patent is hereby corrected as shown below:

Column 19
Line 36, delete "centimeters$_2$" and insert -- centimeters$^2$ --, therefor.
Line 66, delete "Estane$^{TM}$58661" and insert -- Estane$^{TM}$ 58661 --, therefor.
Line 67, delete "Vector$^{TM}$4111." and insert -- Vector$^{TM}$ 4111. --, therefor.

Column 20
Line 1, delete "centimeters$_2$" and insert -- centimeters$^2$ --, therefor.
Line 7, delete "0.254mm" and insert -- 0.254 mm --, therefor.
Line 16, delete "Estane$^{TM}$58661" and insert -- Estane$^{TM}$ 58661 --, therefor.
Line 16, delete "Vector$^{TM}$4111." and insert -- Vector$^{TM}$ 4111. --, therefor.
Line 17, delete "centimeters$_2$" and insert -- centimeters$^2$ --, therefor.
Line 26, delete "Alber" and insert -- Albert --, therefor.
Line 39, delete "Estane 58661" and insert -- Estane$^{TM}$ 58661 --, therefor.
Line 44, delete "Vector 4111" and insert -- Vector$^{TM}$ 4111 --, therefor.

Column 21
Line 59, after "(36.6" insert -- oz/sq. in.) --.
Line 60, below "(20.8 oz/sq. in.)" delete "oz/sq. in.)".
Line 65, delete "meter" and insert -- diameter --, therefor.
Line 66, before "approximately" insert -- was --.
Line 67, after "relatively" insert -- low --.

Column 22
Line 44, delete "Houston,Texas" and insert -- Houston, Texas --, therefor.
Line 65, delete "Ceadar" and insert -- Cedar --, therefor.

Column 23
Line 63, delete "Kenetic" and insert -- Kinetic --, therefor.

UNITED STATES PATENT AND TRADEMARK OFFICE
CERTIFICATE OF CORRECTION

PATENT NO.        : 7,309,519 B2
APPLICATION NO. : 09/982741
DATED             : December 18, 2007
INVENTOR(S)       : Matthew T. Scholz It is certified that error appears in the above-identified patent and that said Letters Patent is hereby corrected as shown below:

Column 25
Line 4, in Claim 1, delete "surfane" and insert -- surface --, therefor.
Line 15, in Claim 1, delete "polyanaides" and insert -- polyamides --, therefor.
Line 15, in Claim 1, delete "jonomeric" and insert -- ionomeric --, therefor.
Line 18, in Claim 1, delete "elastorners" and insert -- elastomers --, therefor.
Line 42, in Claim 5, delete "Within" and insert -- within --, therefor.
Line 43, in Claim 5, delete "affliction" and insert -- of friction --, therefor.
Line 45, in Claim 6, delete "Within" and insert -- within --, therefor.
Line 50, in Claim 8, delete "farther" and insert -- further --, therefor.
Line 57, in Claim 10, delete "farther" and insert -- further --, therefor.

Signed and Sealed this

Seventeenth Day of June, 2008

JON W. DUDAS
*Director of the United States Patent and Trademark Office*